(12) United States Patent
Turovskiy et al.

(10) Patent No.: US 7,311,703 B2
(45) Date of Patent: Dec. 25, 2007

(54) DEVICES AND METHODS FOR COOLING MICROWAVE ANTENNAS

(75) Inventors: Roman Turovskiy, San Francisco, CA (US); Steven Kim, Los Altos, CA (US); Mani Prakash, Campbell, CA (US); Francesca Rossetto, San Francisco, CA (US)

(73) Assignee: Vivant Medical, Inc., Boulder, CO (US)

( * ) Notice: Subject to any disclaimer, the term of this patent is extended or adjusted under 35 U.S.C. 154(b) by 0 days.

(21) Appl. No.: 10/622,800

(22) Filed: Jul. 18, 2003

(65) Prior Publication Data

US 2005/0015081 A1    Jan. 20, 2005

(51) Int. Cl.
A61B 18/04 (2006.01)
(52) U.S. Cl. ...................................................... 606/33
(58) Field of Classification Search ............ 606/27–52, 606/20–26
See application file for complete search history.

(56) References Cited

U.S. PATENT DOCUMENTS

| | | |
|---|---|---|
| 2,022,065 A | 11/1935 | Wappler |
| 2,047,535 A | 7/1936 | Wappler |
| 3,320,341 A | 5/1967 | Mackie William |
| 3,330,278 A | 7/1967 | Santomieri |
| 3,351,463 A | 11/1967 | Rozner et al. |
| 3,516,412 A | 6/1970 | Ackerman |
| 3,714,851 A | 2/1973 | Orser |
| 3,753,700 A | 8/1973 | Harrison et al. |
| 3,890,977 A | 6/1975 | Wilson |
| 4,010,756 A | 3/1977 | DuMont et al. |
| 4,103,690 A | 8/1978 | Harris |
| 4,140,130 A * | 2/1979 | Storm, III .................... 607/154 |
| 4,274,408 A | 6/1981 | Nimrod |
| 4,311,154 A | 1/1982 | Sterzer et al. |
| 4,341,226 A | 7/1982 | Peters |

(Continued)

FOREIGN PATENT DOCUMENTS

EP    0 385 604 A2    9/1990

(Continued)

OTHER PUBLICATIONS

Chou, C.K. (1995). "Radiofrequency Hyperthermia in Cancer Therapy," Chapter 94 *In Biologic Effects of Nonionizing Electromagnetic Fields.* CRC Press, Inc. pp. 1424-1428.

(Continued)

*Primary Examiner*—Michael Peffley
*Assistant Examiner*—Pete Vrettakos

(57) ABSTRACT

Devices and methods for cooling microwave antennas are disclosed herein. The cooling systems can be used with various types of microwave antennas. One variation generally comprises a handle portion with an elongate outer jacket extending from the handle portion. A microwave antenna is positioned within the handle and outer jacket such that cooling fluid pumped into the handle comes into contact directly along a portion of the length, or a majority of the length, or the entire length of the antenna to allow for direct convective cooling. Other variations include cooling sheaths which form defined cooling channels around a portion of the antenna. Yet another variation includes passively-cooled systems which utilize expandable balloons to urge tissue away from the surface of the microwave antenna as well as cooling sheaths which are cooled through endothermic chemical reactions. Furthermore, the microwave antennas themselves can have cooling lumens integrated directly therethrough.

24 Claims, 29 Drawing Sheets

U.S. PATENT DOCUMENTS

| | | |
|---|---|---|
| 4,402,328 A | 9/1983 | Doring |
| 4,557,272 A | 12/1985 | Carr |
| 4,592,356 A | 6/1986 | Gutierrez |
| 4,595,007 A | 6/1986 | Mericle |
| 4,612,940 A | 9/1986 | Kasevich et al. |
| 4,616,656 A | 10/1986 | Nicholson et al. |
| 4,621,642 A | 11/1986 | Chen |
| 4,633,880 A | 1/1987 | Osypka et al. |
| 4,658,836 A | 4/1987 | Turner |
| 4,665,906 A | 5/1987 | Jervis |
| 4,682,606 A | 7/1987 | DeCaprio |
| 4,700,716 A | 10/1987 | Kasevich et al. |
| 4,776,086 A | 10/1988 | Kasevich et al. |
| 4,799,495 A | 1/1989 | Hawkins et al. |
| 4,800,899 A | 1/1989 | Elliott |
| 4,869,259 A | 9/1989 | Elkins |
| 4,925,445 A | 5/1990 | Sakamoto et al. |
| 4,966,583 A | 10/1990 | Debbas |
| 5,011,473 A | 4/1991 | Gatturna |
| 5,018,530 A | 5/1991 | Rank et al. |
| 5,059,197 A | 10/1991 | Urie et al. |
| 5,067,957 A | 11/1991 | Jervis |
| 5,122,136 A | 6/1992 | Guglielmi et al. |
| 5,158,084 A | 10/1992 | Ghiatas |
| 5,183,463 A | 2/1993 | Debbas |
| 5,190,054 A | 3/1993 | Fetter et al. |
| 5,190,546 A | 3/1993 | Jervis |
| 5,197,482 A | 3/1993 | Rank et al. |
| 5,205,829 A | 4/1993 | Lituchy |
| 5,217,027 A | 6/1993 | Hermens |
| 5,221,269 A | 6/1993 | Miller et al. |
| 5,246,438 A | 9/1993 | Langberg |
| 5,249,585 A | 10/1993 | Turner et al. |
| 5,281,217 A * | 1/1994 | Edwards et al. .............. 606/41 |
| 5,282,845 A | 2/1994 | Bush et al. |
| 5,300,068 A | 4/1994 | Rosar et al. |
| 5,301,682 A | 4/1994 | Debbas |
| 5,314,466 A | 5/1994 | Stern et al. |
| 5,344,441 A | 9/1994 | Gronauer |
| 5,348,554 A | 9/1994 | Imran et al. |
| 5,350,419 A | 9/1994 | Bendel et al. |
| 5,353,804 A | 10/1994 | Kornberg et al. |
| 5,370,644 A | 12/1994 | Langberg |
| 5,405,346 A | 4/1995 | Grundy et al. |
| 5,409,004 A | 4/1995 | Sloan |
| 5,462,062 A | 10/1995 | Rubinstein et al. |
| 5,472,441 A | 12/1995 | Edwards et al. |
| 5,486,183 A | 1/1996 | Middleman et al. |
| 5,488,958 A | 2/1996 | Topel et al. |
| 5,500,012 A | 3/1996 | Brucker et al. |
| 5,507,743 A | 4/1996 | Edwards et al. |
| 5,520,684 A | 5/1996 | Imran |
| 5,536,267 A | 7/1996 | Edwards et al. |
| 5,540,683 A | 7/1996 | Ichikawa et al. |
| 5,556,377 A | 9/1996 | Rosen et al. |
| 5,556,410 A | 9/1996 | Mittermeir et al. |
| 5,558,673 A | 9/1996 | Edwards et al. |
| 5,599,294 A | 2/1997 | Edwards et al. |
| 5,609,151 A | 3/1997 | Mulier et al. |
| 5,672,173 A | 9/1997 | Gough et al. |
| 5,672,174 A | 9/1997 | Gough et al. |
| 5,683,384 A | 11/1997 | Gough et al. |
| 5,685,853 A | 11/1997 | Bonnet |
| 5,700,243 A | 12/1997 | Narciso, Jr. |
| 5,709,697 A | 1/1998 | Ratcliff et al. |
| 5,720,718 A | 2/1998 | Rosen et al. |
| 5,735,847 A | 4/1998 | Gough et al. |
| 5,741,225 A | 4/1998 | Lax et al. |
| 5,749,887 A | 5/1998 | Heske et al. |
| 5,776,176 A | 7/1998 | Rudie |
| 5,794,626 A | 8/1998 | Kieturakis |
| 5,795,308 A | 8/1998 | Russin |
| 5,800,484 A | 9/1998 | Gough et al. |
| 5,800,486 A | 9/1998 | Thome et al. |
| 5,807,339 A | 9/1998 | Bostrom et al. |
| 5,810,804 A | 9/1998 | Gough et al. |
| 5,829,519 A * | 11/1998 | Uthe ............................ 166/60 |
| 5,853,366 A | 12/1998 | Dowlatshahi |
| 5,855,576 A | 1/1999 | LeVeen et al. |
| 5,863,290 A | 1/1999 | Gough et al. |
| 5,871,523 A | 2/1999 | Fleischman et al. |
| 5,879,357 A | 3/1999 | Heaton et al. |
| 5,882,316 A | 3/1999 | Chu et al. |
| 5,897,554 A | 4/1999 | Chia et al. |
| 5,902,251 A * | 5/1999 | vanHooydonk ............. 600/549 |
| 5,902,310 A | 5/1999 | Foerster et al. |
| 5,904,690 A | 5/1999 | Middleman et al. |
| 5,904,691 A | 5/1999 | Barnett et al. |
| 5,904,709 A | 5/1999 | Arndt et al. |
| 5,938,692 A | 8/1999 | Rudie |
| 5,941,890 A | 8/1999 | Voegele et al. |
| 5,951,546 A | 9/1999 | Lorentzen |
| 5,951,547 A * | 9/1999 | Gough et al. ................. 606/41 |
| 5,954,655 A | 9/1999 | Hussman |
| 5,954,719 A | 9/1999 | Chen et al. |
| 5,957,969 A | 9/1999 | Warner et al. |
| 5,964,755 A * | 10/1999 | Edwards ..................... 606/41 |
| 5,974,343 A | 10/1999 | Brevard et al. |
| 5,980,563 A | 11/1999 | Tu et al. |
| 5,989,265 A | 11/1999 | Bouquet De La Joliniere et al. |
| 6,007,495 A | 12/1999 | Matula |
| 6,016,811 A | 1/2000 | Knopp et al. |
| 6,019,757 A | 2/2000 | Scheldrup |
| 6,022,362 A | 2/2000 | Lee et al. |
| 6,026,331 A | 2/2000 | Feldberg et al. |
| 6,027,524 A | 2/2000 | Petit |
| 6,032,078 A | 2/2000 | Rudie |
| 6,039,735 A | 3/2000 | Greep |
| 6,050,954 A | 4/2000 | Mittermeier |
| 6,051,008 A | 4/2000 | Saadat et al. |
| 6,053,876 A | 4/2000 | Fisher |
| 6,053,925 A | 4/2000 | Barnhart |
| 6,056,744 A | 5/2000 | Edwards |
| 6,059,780 A | 5/2000 | Gough et al. |
| 6,073,051 A | 6/2000 | Sharkey et al. |
| 6,080,113 A | 6/2000 | Heneveld et al. |
| 6,080,114 A | 6/2000 | Russin |
| 6,080,150 A | 6/2000 | Gough |
| 6,097,985 A | 8/2000 | Kasevich et al. |
| 6,106,518 A | 8/2000 | Wittenberger et al. |
| 6,122,551 A | 9/2000 | Rudie et al. |
| 6,134,476 A | 10/2000 | Arndt et al. |
| 6,146,379 A | 11/2000 | Fleischman et al. |
| 6,146,657 A | 11/2000 | Unger |
| 6,176,856 B1 | 1/2001 | Jandak et al. |
| 6,181,970 B1 | 1/2001 | Kasevich |
| 6,217,528 B1 | 4/2001 | Koblish et al. |
| 6,223,086 B1 | 4/2001 | Carl et al. |
| 6,233,490 B1 | 5/2001 | Kasevich |
| 6,245,064 B1 | 6/2001 | Lesh et al. |
| 6,245,318 B1 | 6/2001 | Klibanov et al. |
| 6,251,128 B1 | 6/2001 | Knopp et al. |
| 6,275,738 B1 | 8/2001 | Kasevich et al. |
| 6,277,113 B1 | 8/2001 | Berube |
| 6,290,715 B1 | 9/2001 | Sharkey et al. |
| 6,306,132 B1 | 10/2001 | Moorman et al. |
| 6,325,796 B1 | 12/2001 | Berube et al. |
| 6,330,479 B1 | 12/2001 | Stauffer |
| 6,346,104 B2 | 2/2002 | Daly et al. |
| 6,347,251 B1 | 2/2002 | Deng |
| 6,355,033 B1 | 3/2002 | Moorman et al. |
| 6,405,733 B1 | 6/2002 | Fogarty et al. |
| 6,471,696 B1 | 10/2002 | Berube et al. |
| 6,496,737 B2 * | 12/2002 | Rudie et al. ................ 607/101 |

| | | | | | | |
|---|---|---|---|---|---|---|
| 6,496,738 | B2 | 12/2002 | Carr | WO | WO 93/20768 | 10/1993 |
| 6,514,251 | B1 | 2/2003 | Ni et al. | WO | WO 96/27328 | 9/1996 |
| 6,530,922 | B2 | 3/2003 | Cosman et al. | WO | WO 96/34571 | 11/1996 |
| 6,551,311 | B2 | 4/2003 | Lee et al. | WO | WO 97/48449 | 12/1997 |
| 6,564,806 | B1 | 5/2003 | Fogarty et al. | WO | WO 97/48450 | 12/1997 |
| 6,569,159 | B1 | 5/2003 | Edwards et al. | WO | WO 97/48451 | 12/1997 |
| 6,611,699 | B2 | 8/2003 | Messing | WO | WO 99/04704 | 2/1999 |
| 6,622,731 | B2 | 9/2003 | Daniel et al. | WO | WO 99/25248 | 5/1999 |
| 6,663,624 | B2 | 12/2003 | Edwards et al. | WO | WO 99/43268 | 9/1999 |
| 6,685,700 | B2 | 2/2004 | Behl et al. | WO | WO 99/44506 | 9/1999 |
| 6,699,241 | B2 | 3/2004 | Rappaport et al. | WO | WO 99/56642 | 11/1999 |
| 6,722,371 | B1 | 4/2004 | Fogarty et al. | WO | WO 99/56643 | 11/1999 |
| 6,752,154 | B2 | 6/2004 | Fogarty et al. | WO | WO 99/56812 | 11/1999 |
| 6,752,767 | B2 | 6/2004 | Turovskiy et al. | WO | WO 99/58065 | 11/1999 |
| 6,878,147 | B2 | 4/2005 | Prakash et al. | WO | WO 99/66834 | 12/1999 |
| 2001/0001819 | A1 | 5/2001 | Lee et al. | WO | WO 00/10471 | 3/2000 |
| 2001/0037812 | A1 | 11/2001 | Dobak, III et al. | WO | WO 00/12009 | 3/2000 |
| 2001/0051131 | A1 | 12/2001 | Unger | WO | WO 00/12010 | 3/2000 |
| 2002/0022832 | A1 | 2/2002 | Mikus et al. | WO | WO 00/13602 | 3/2000 |
| 2002/0059938 | A1 | 5/2002 | Fogarty et al. | WO | WO 00/16697 | 3/2000 |
| 2002/0087151 | A1 | 7/2002 | Mody et al. | WO | WO 00/24320 | 5/2000 |
| 2002/0133148 | A1 | 9/2002 | Daniel et al. | WO | WO 00/28913 | 5/2000 |
| 2002/0198520 | A1 | 12/2002 | Coen et al. | WO | WO 00/30531 | 6/2000 |
| 2003/0004506 | A1 | 1/2003 | Messing | WO | WO 00/33743 | 6/2000 |
| 2003/0065317 | A1 | 4/2003 | Rudie et al. | WO | WO 00/49957 | 8/2000 |
| 2003/0069578 | A1 | 4/2003 | Hall et al. | WO | WO 00/57811 | 10/2000 |
| 2003/0088242 | A1 | 5/2003 | Prakash et al. | WO | WO 01/05317 A1 | 1/2001 |
| 2003/0109862 | A1 | 6/2003 | Prakash et al. | WO | WO 01/05320 A1 | 1/2001 |
| 2003/0195499 | A1 | 10/2003 | Prakash et al. | WO | WO 01/60235 | 8/2001 |
| 2003/0208199 | A1 | 11/2003 | Keane | WO | WO 03/034932 | 5/2003 |
| 2004/0168692 | A1 | 9/2004 | Fogarty et al. | WO | WO 03/039385 | 5/2003 |
| 2004/0267156 | A1 | 12/2004 | Turovskiy et al. | WO | WO 03/088806 A3 | 10/2003 |
| 2005/0015081 | A1 | 1/2005 | Turovskiy et al. | WO | WO 03/088858 A1 | 10/2003 |
| 2005/0062666 | A1 | 3/2005 | Prakash et al. | WO | WO 2005/011049 A3 | 2/2005 |

FOREIGN PATENT DOCUMENTS

| | | |
|---|---|---|
| EP | 0 395 997 A1 | 11/1990 |
| EP | 0 667 126 | 8/1995 |
| EP | 0 829 232 A2 | 3/1998 |
| WO | WO 88/06864 | 9/1988 |
| WO | WO 92/12678 | 8/1992 |
| WO | WO 93/20767 | 10/1993 |

OTHER PUBLICATIONS

Urologix, Inc.—Medical Professionals: Targis™ Technology (Date Unknown). "Overcoming the Challenge" located at: <http://www.urologix.com/medical/technology.html> last visited on Apr. 27, 2001. Three pages.

* cited by examiner

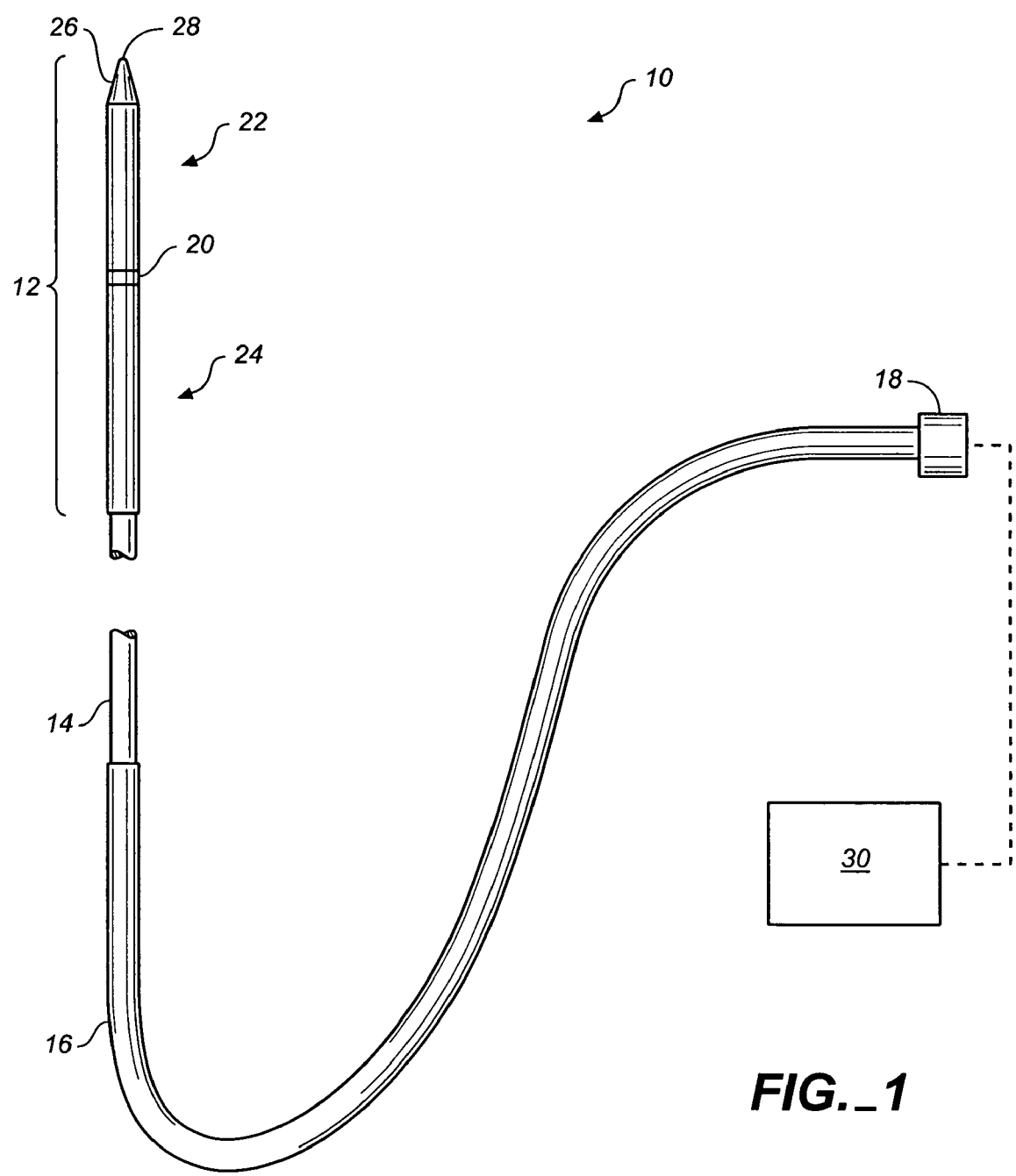
FIG._1

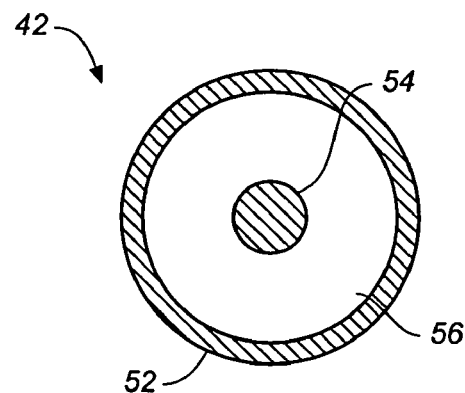
FIG._2A
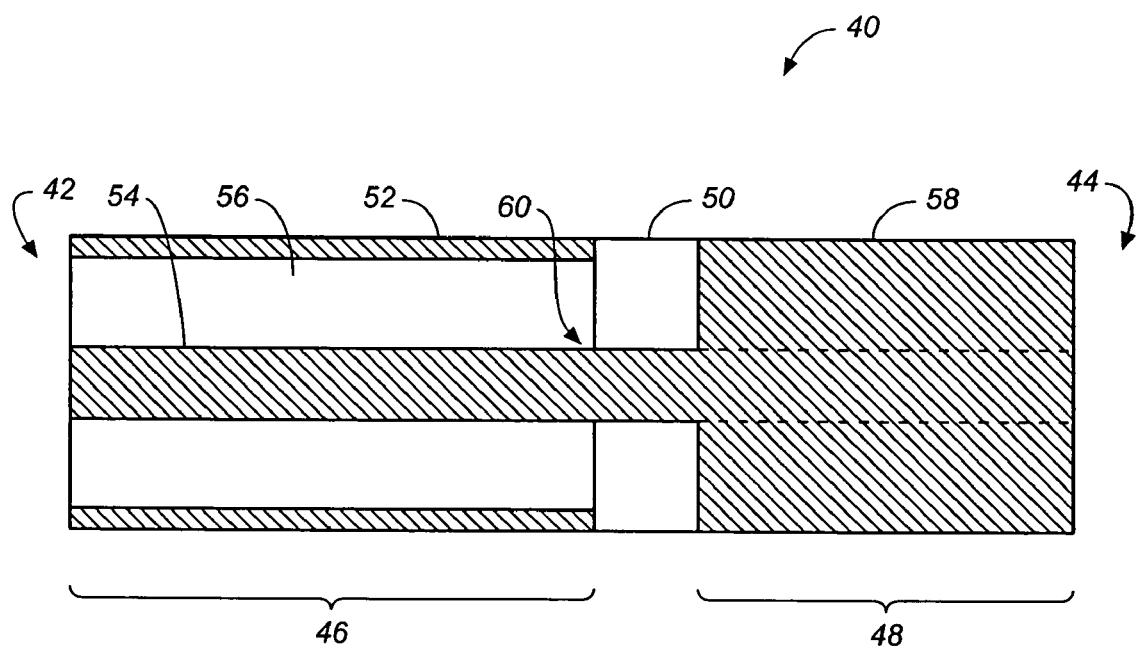
FIG._2B

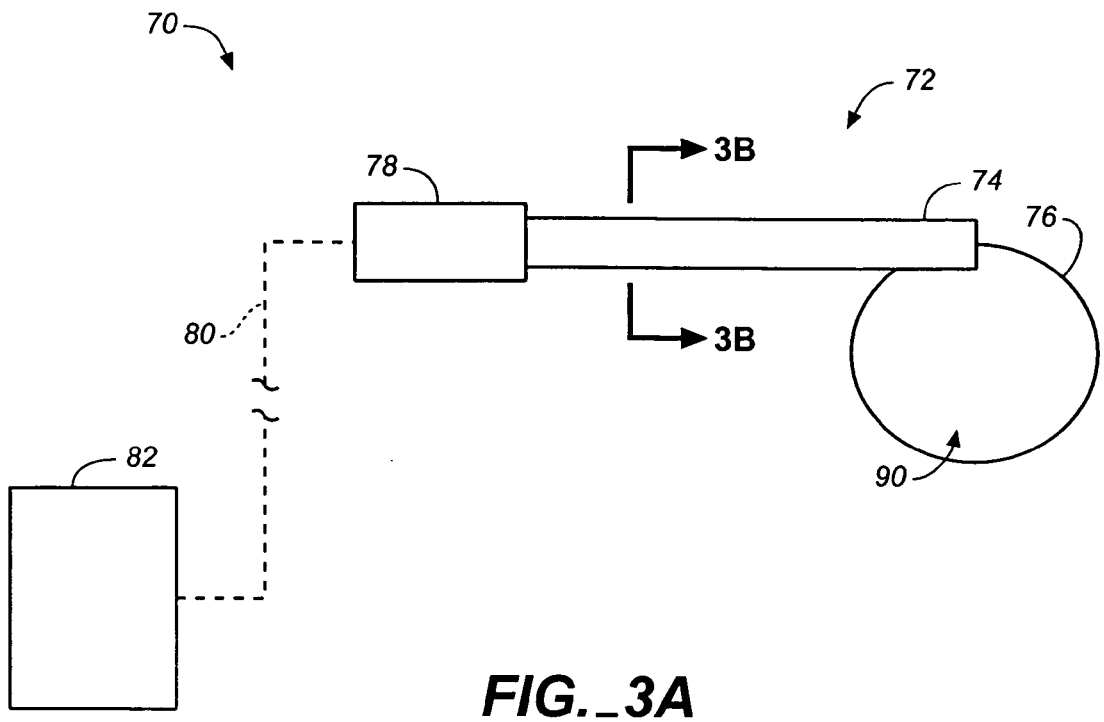
FIG._3A
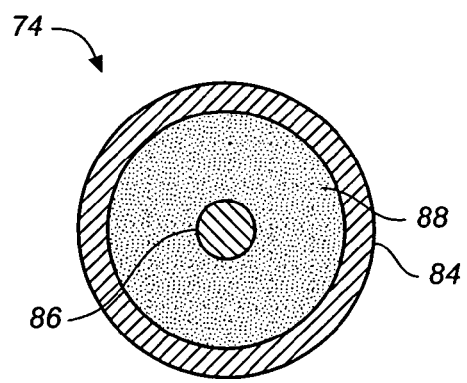
FIG._3B

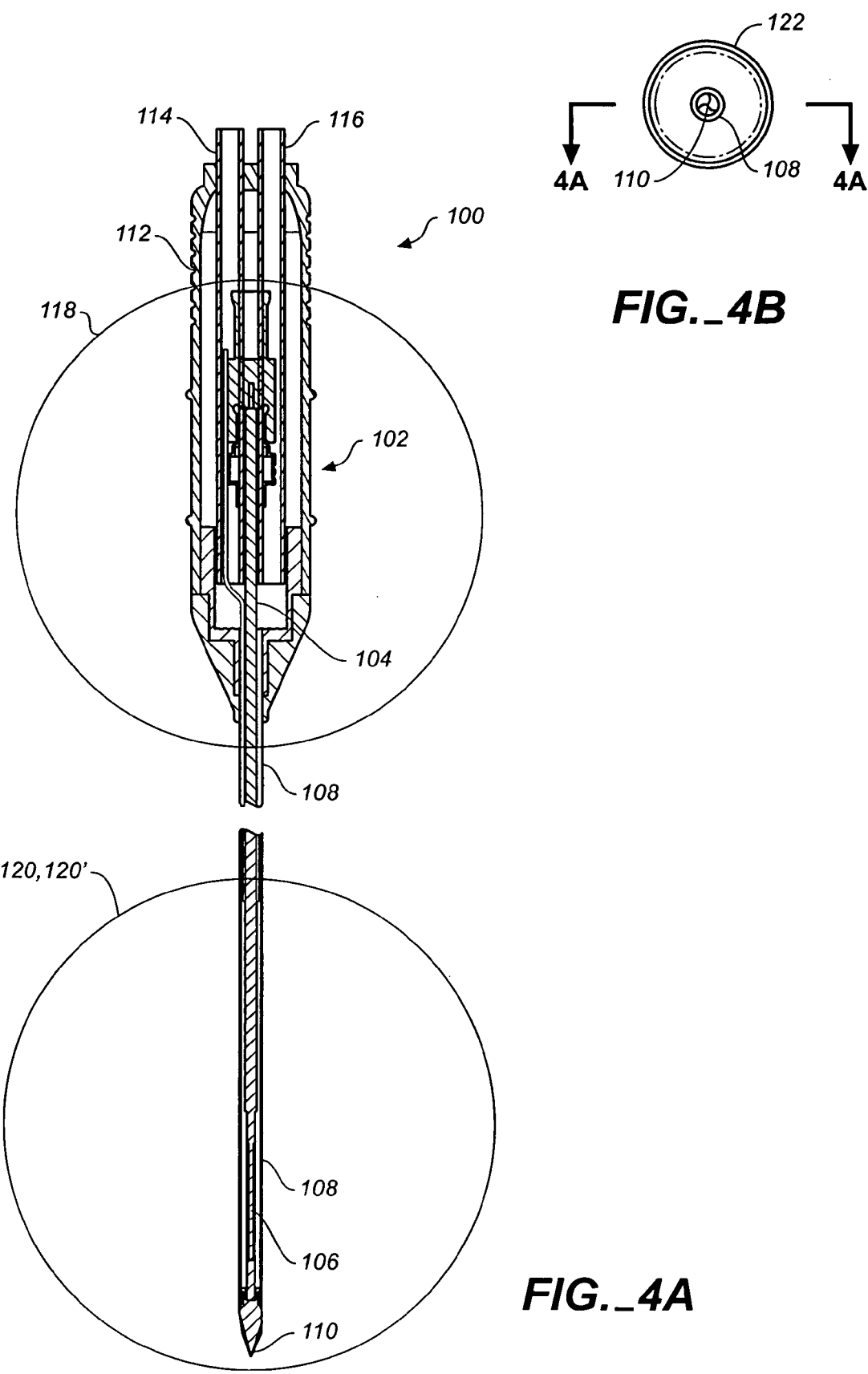
FIG._4B
FIG._4A

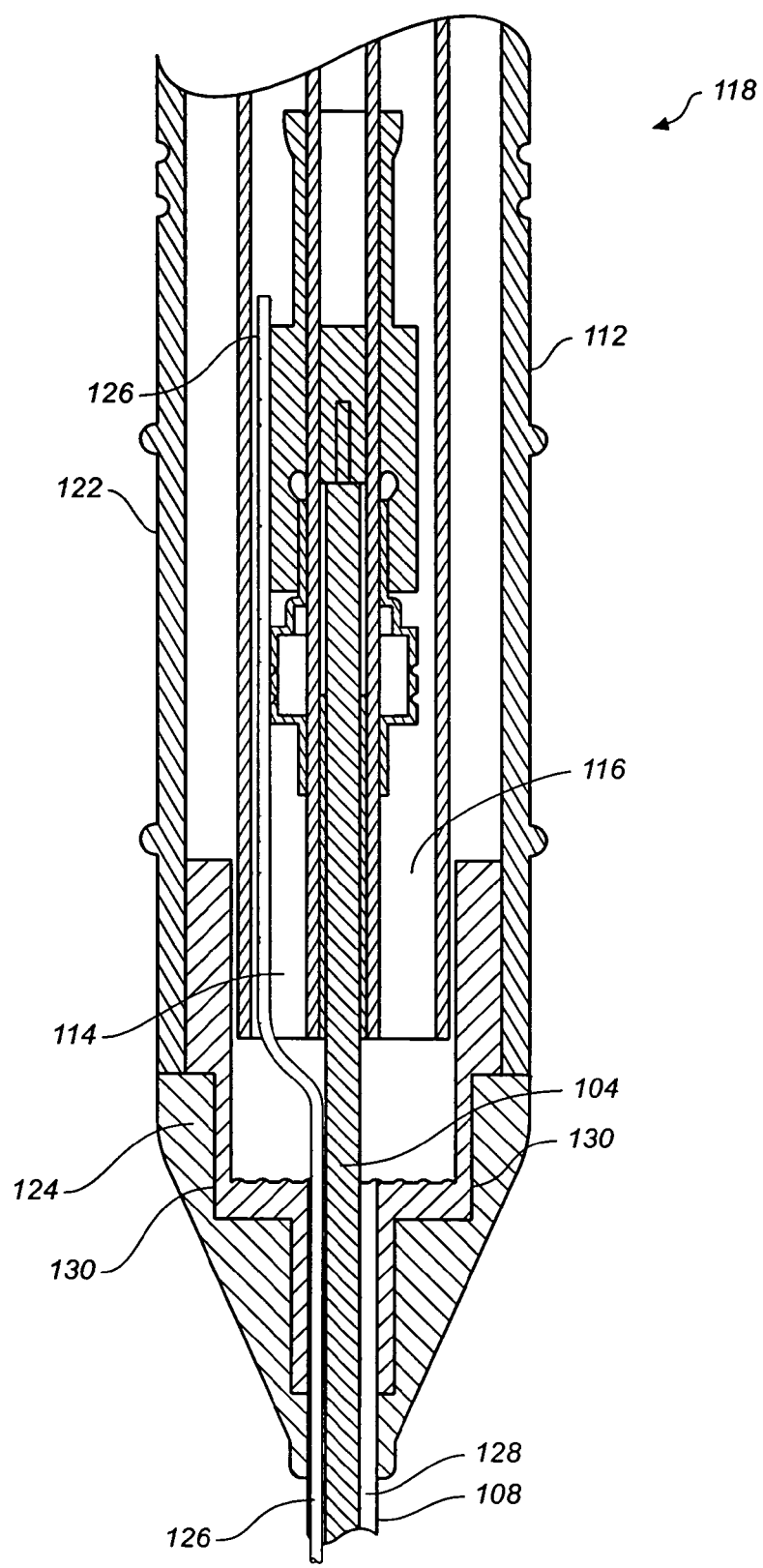
FIG._4C

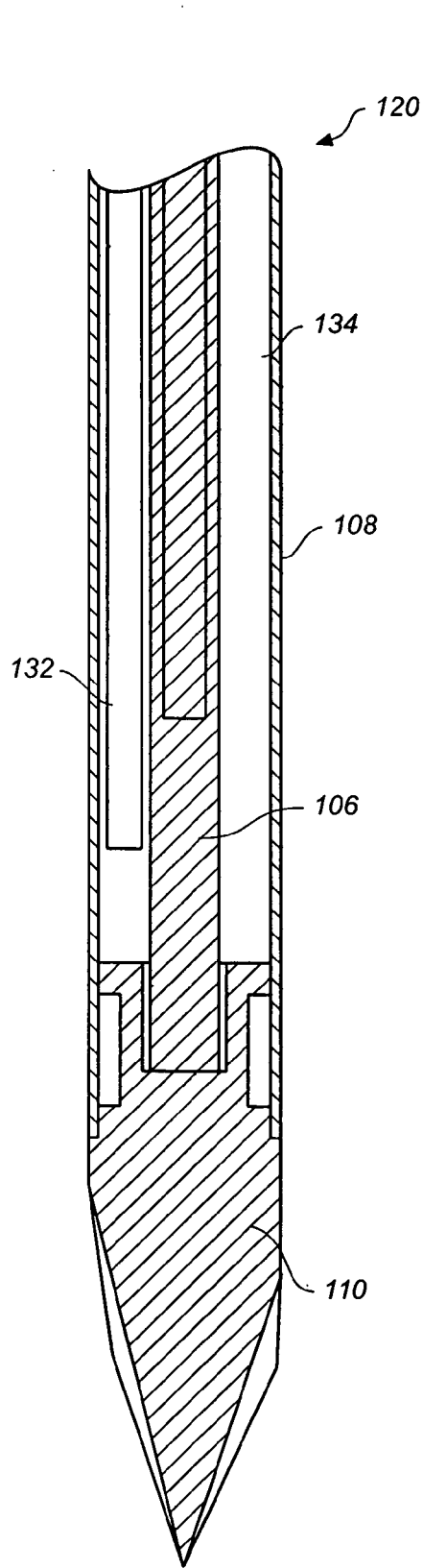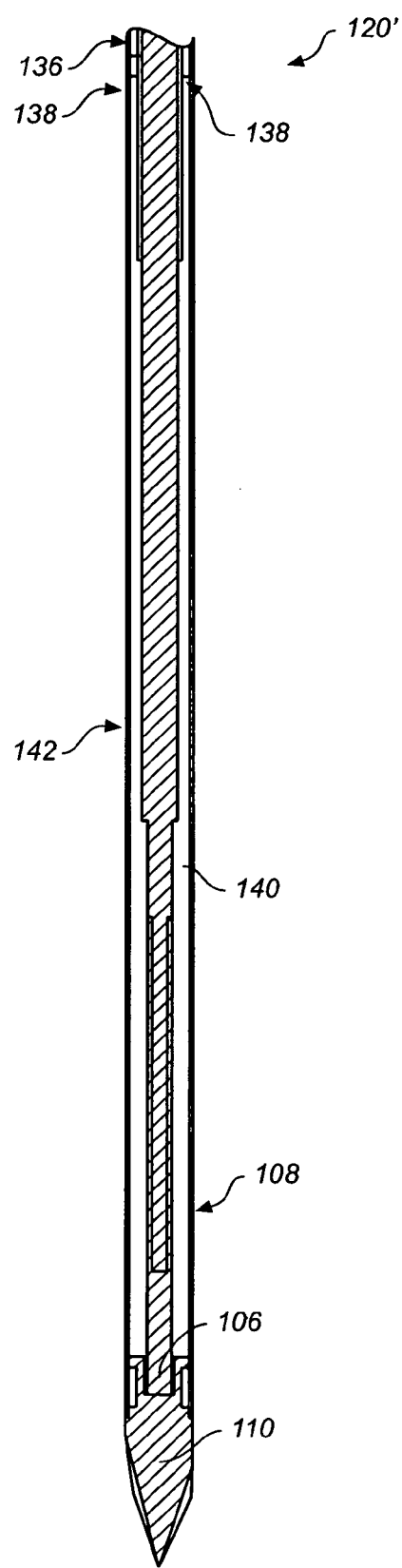
FIG._4D  FIG._4E

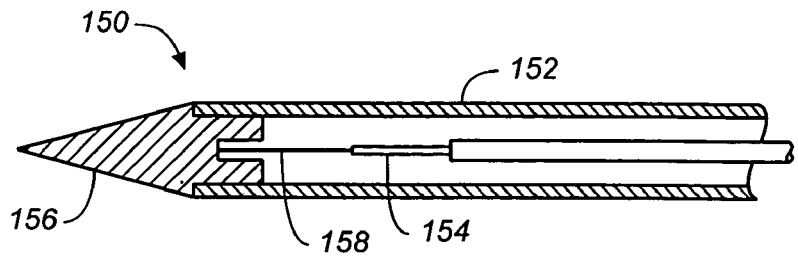
FIG._5A
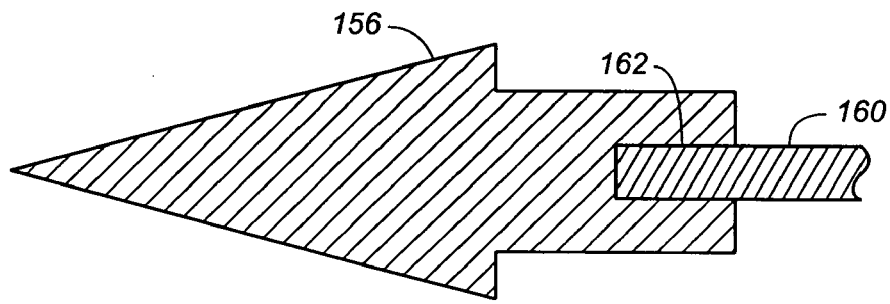
FIG._5B
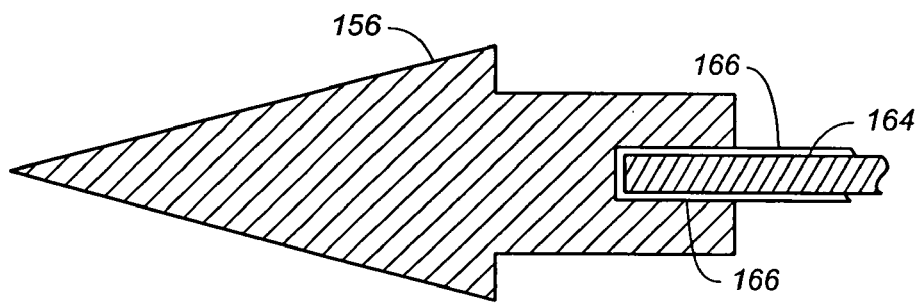
FIG._5C
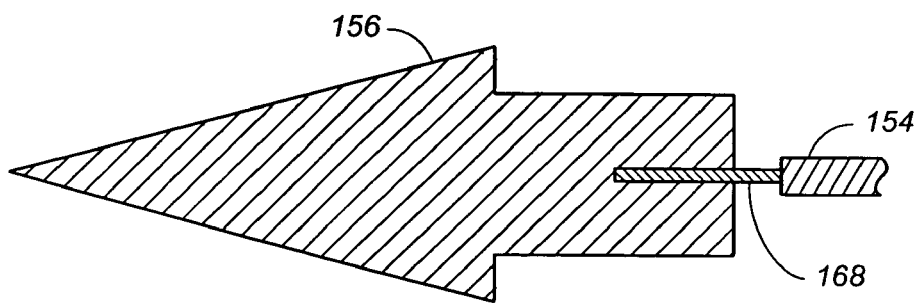
FIG._5D

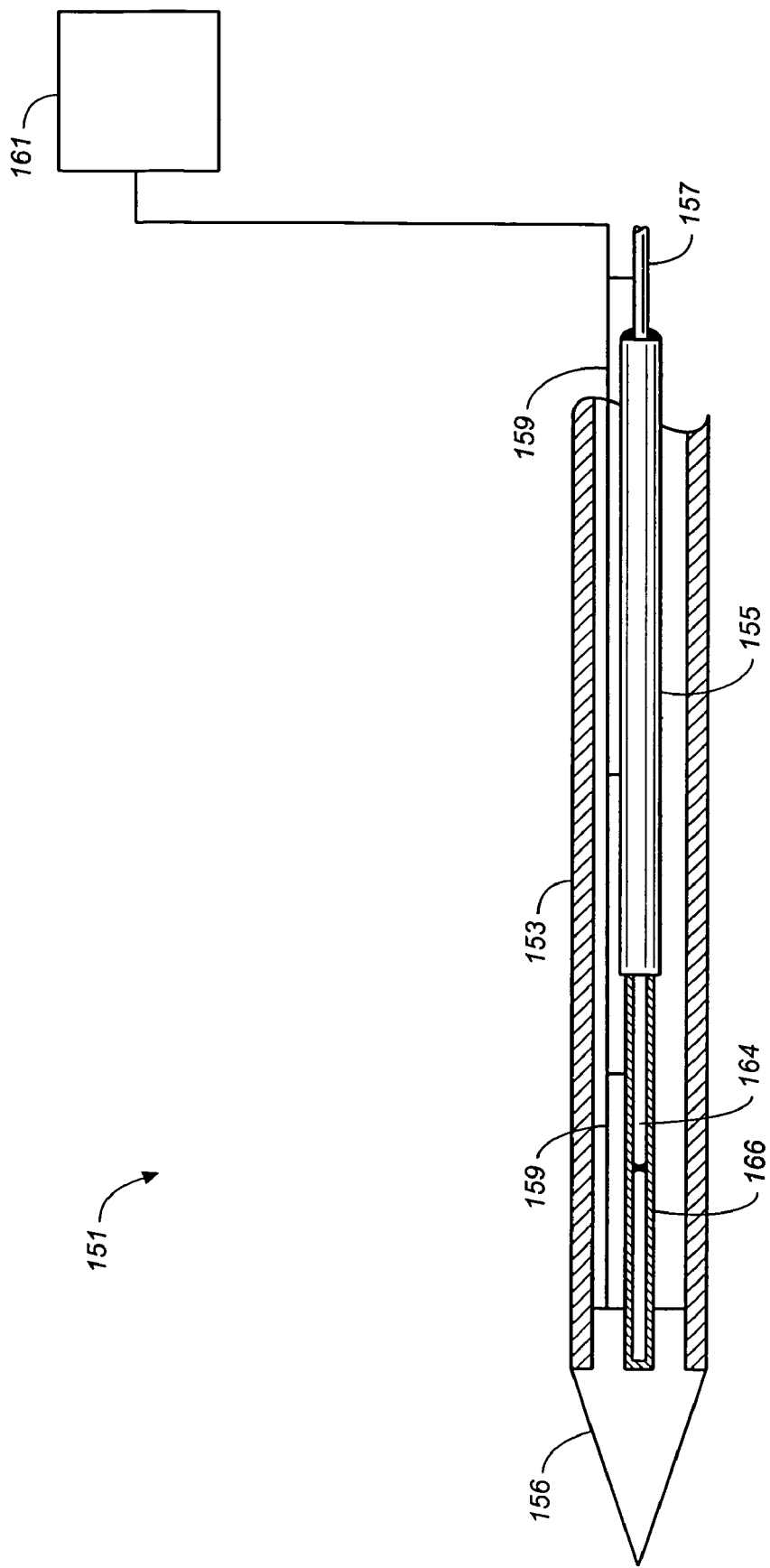
FIG._5E

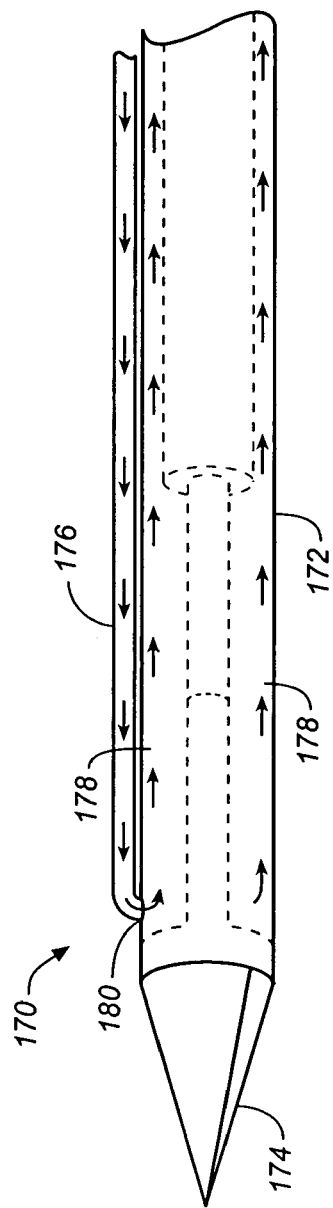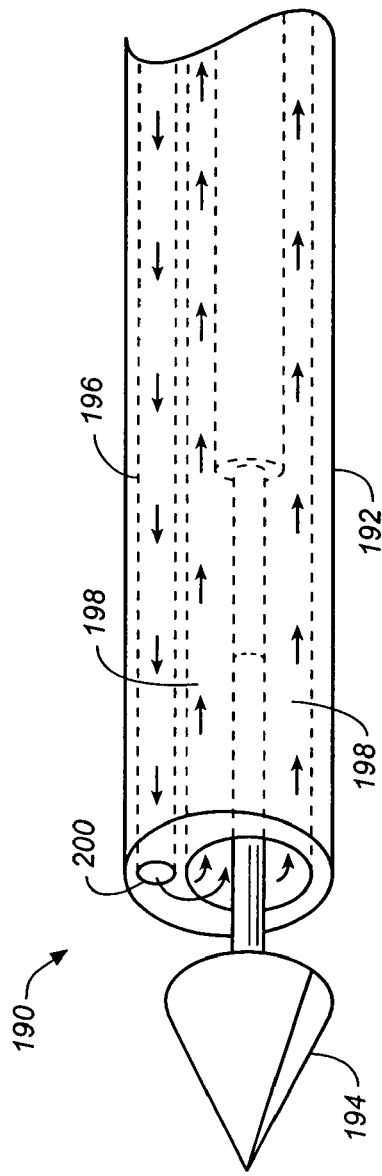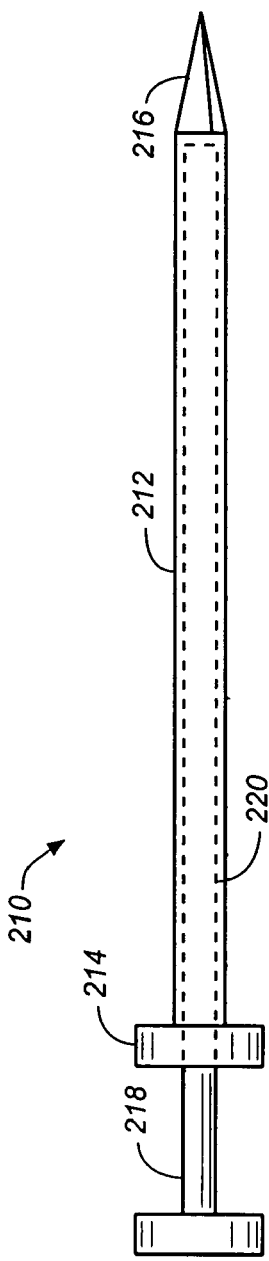

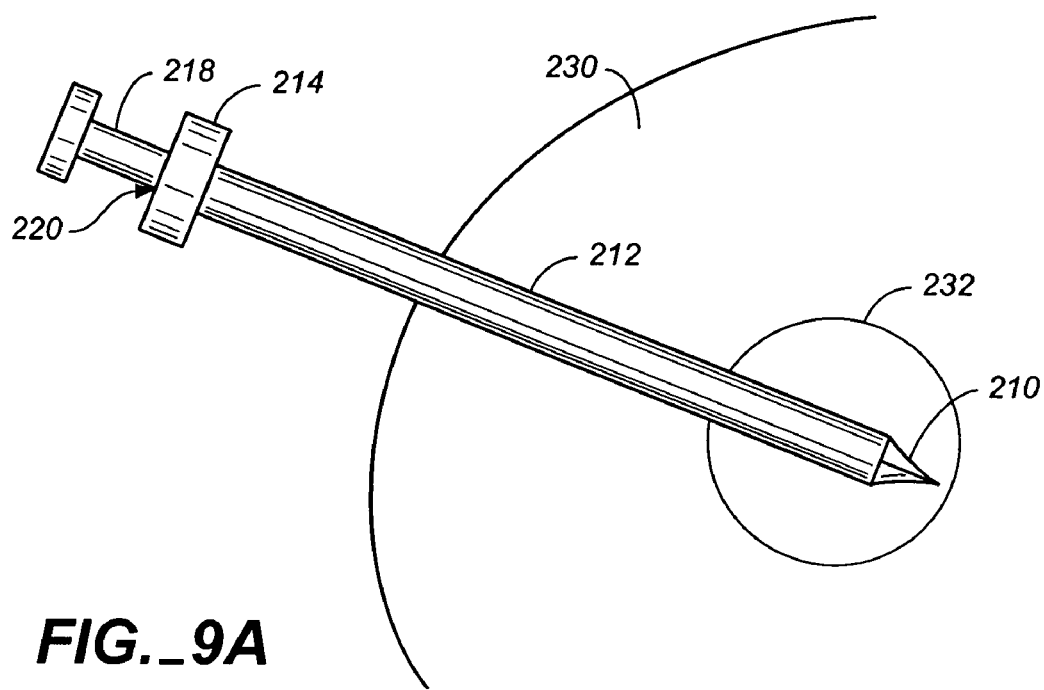
FIG._9A
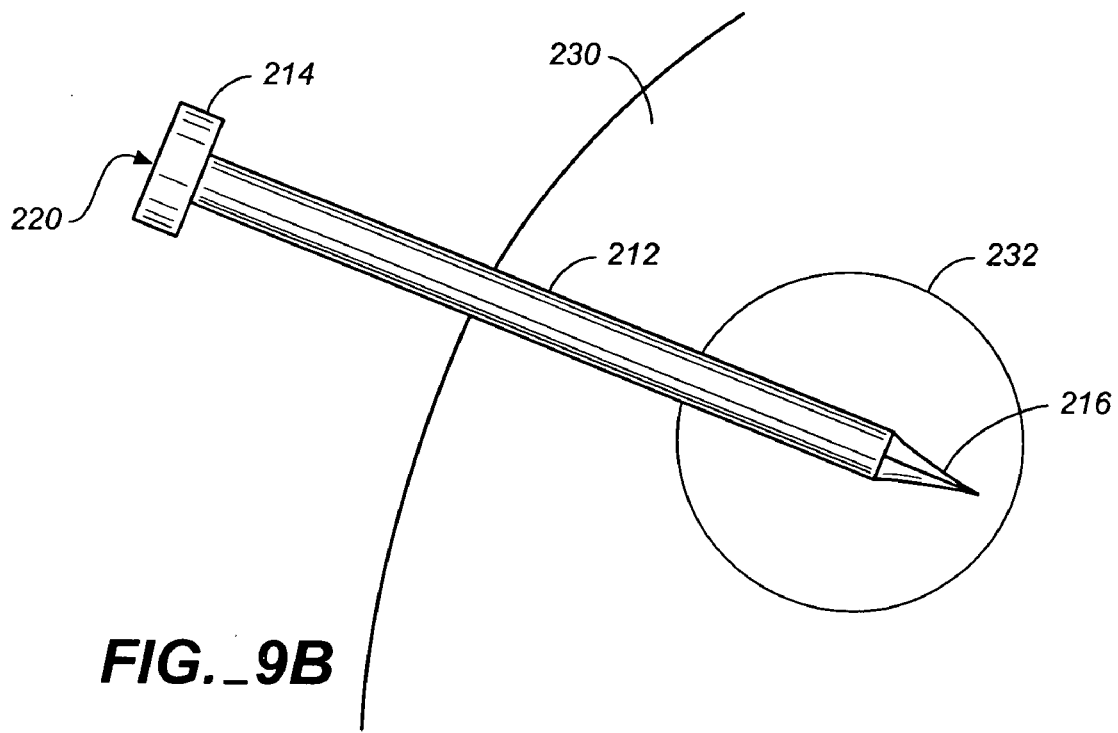
FIG._9B

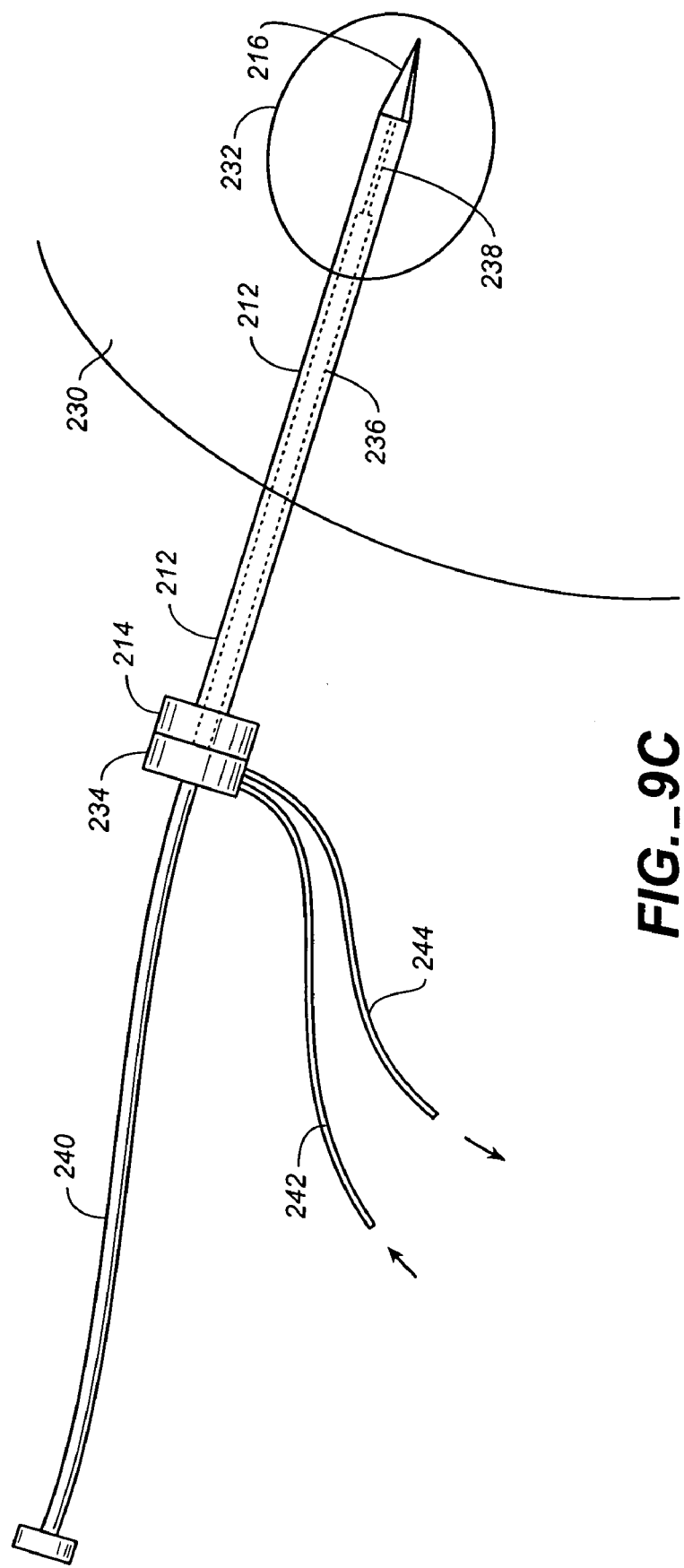
FIG._9C

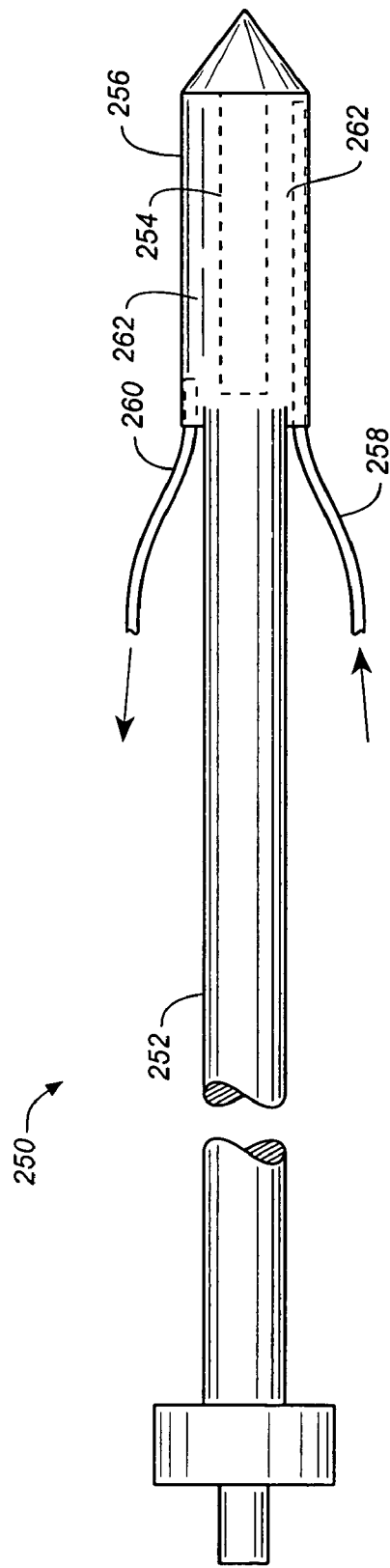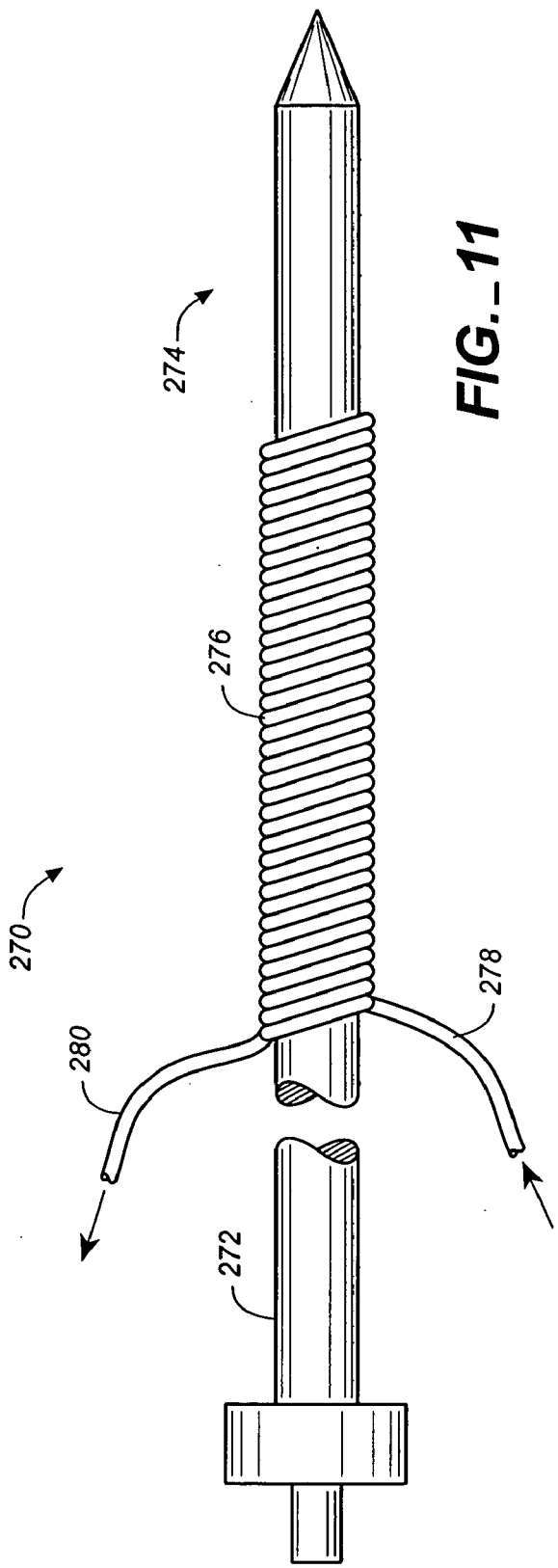

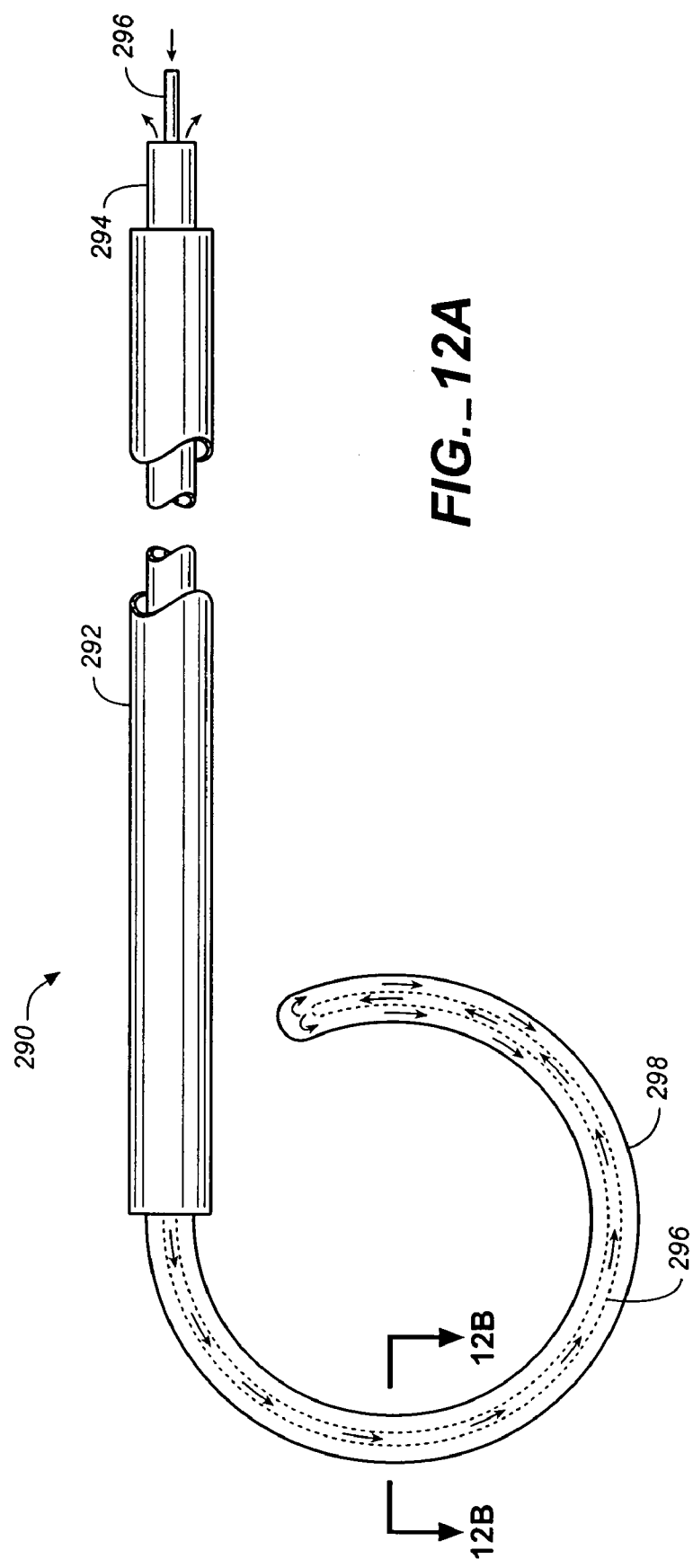
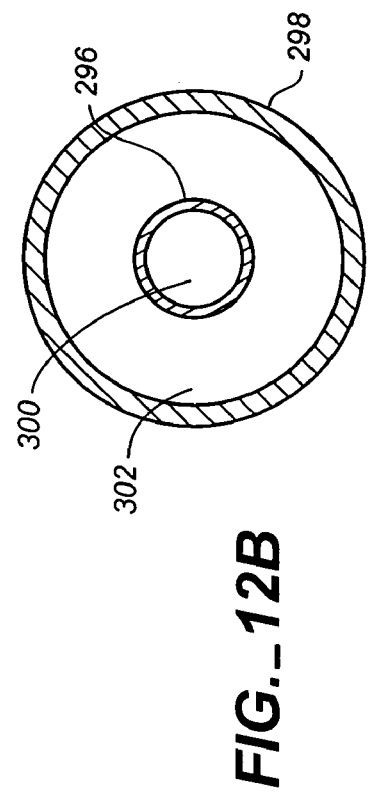
FIG._12A
FIG._12B

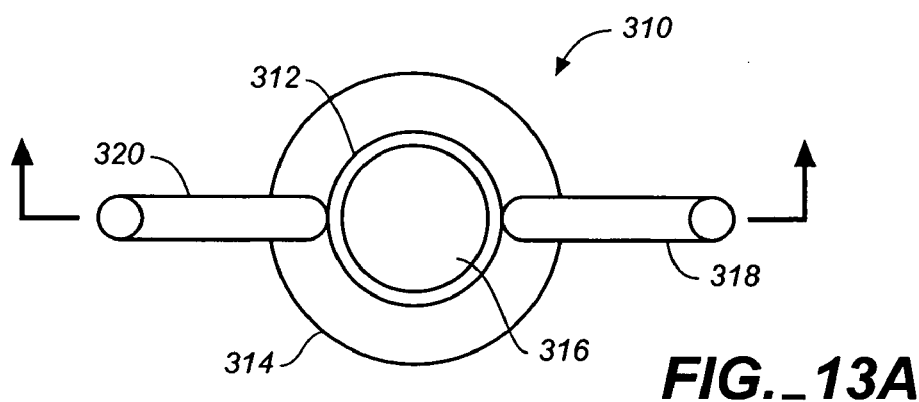
FIG._13A
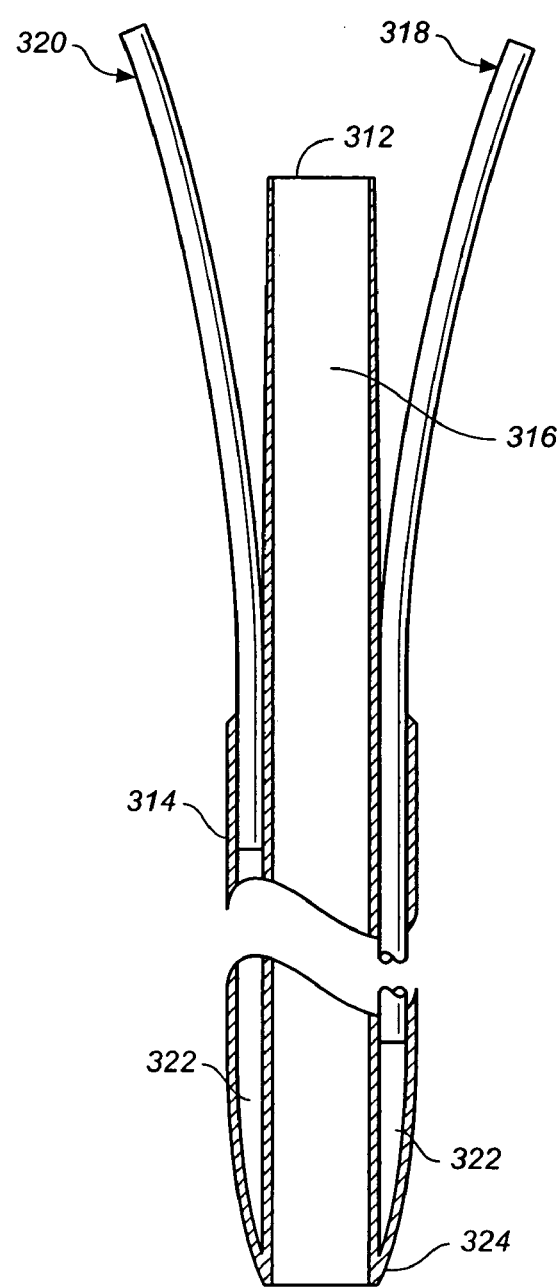
FIG._13B

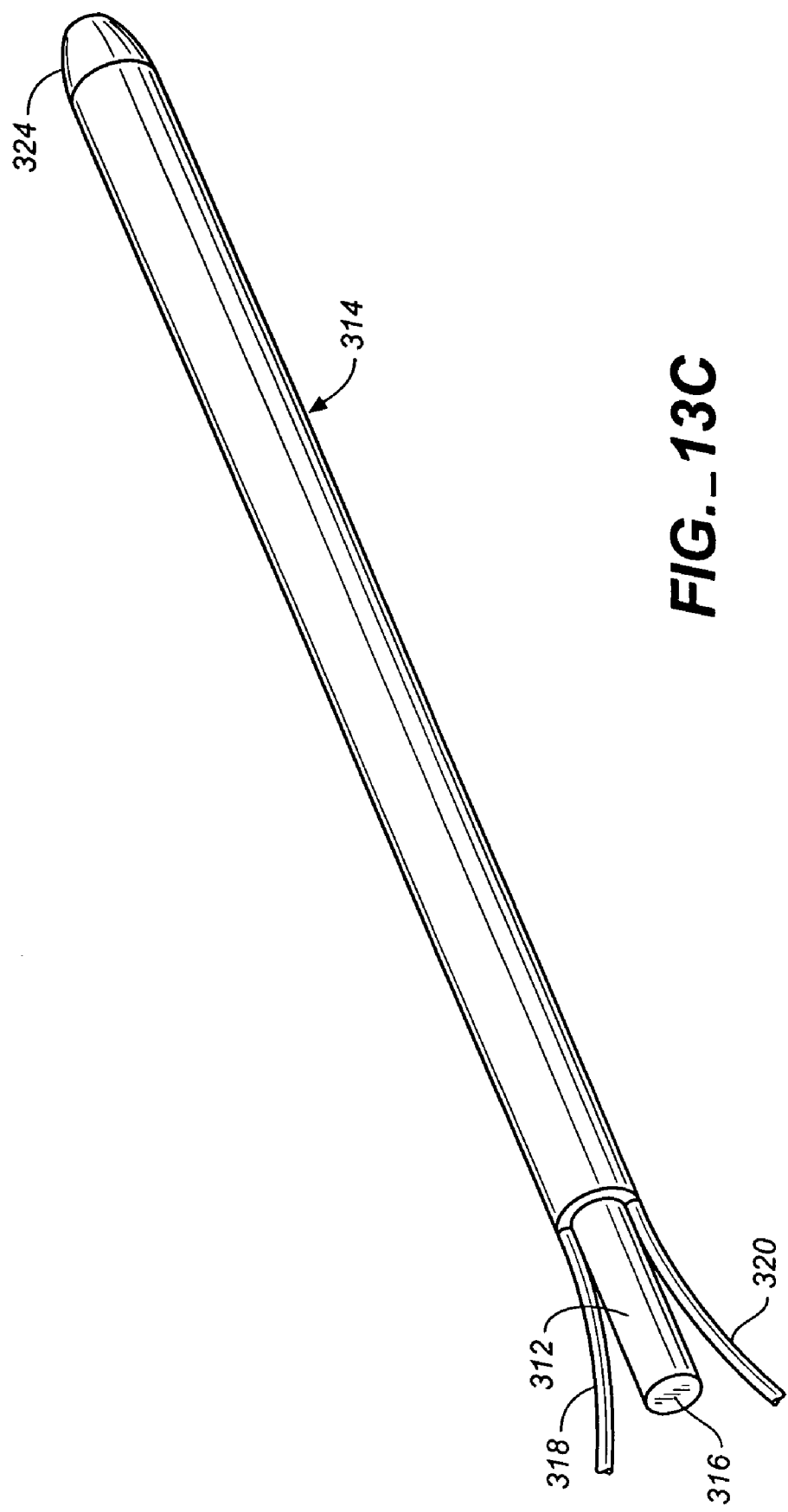

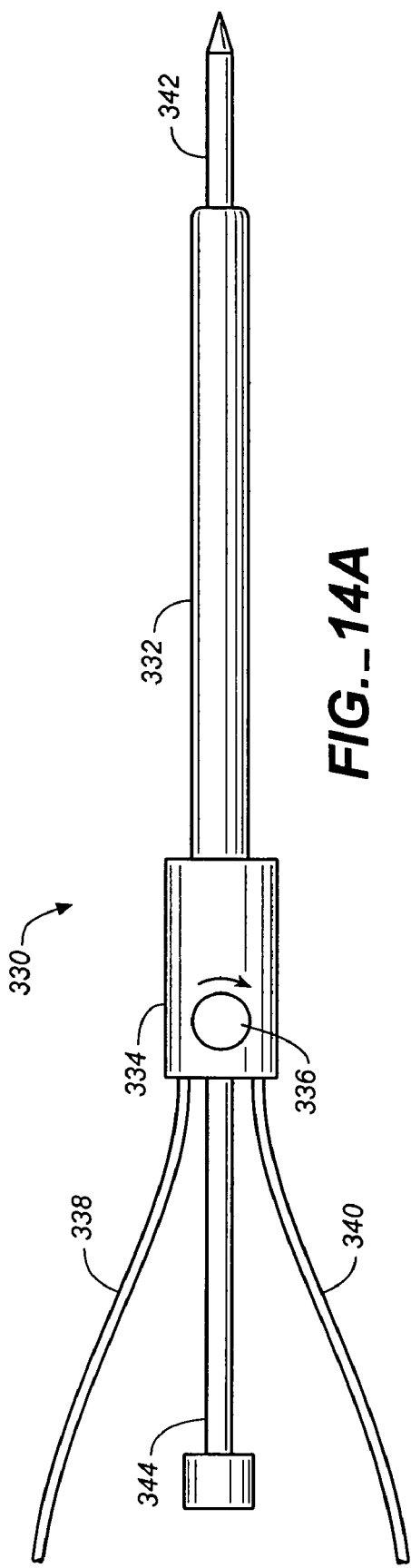
FIG._14A
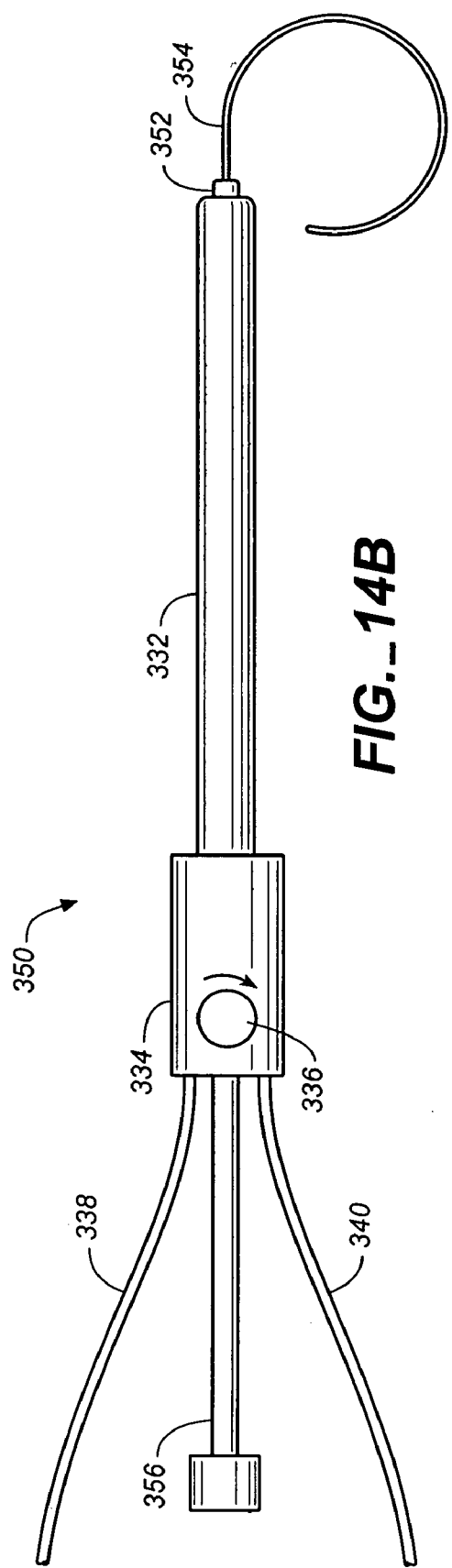
FIG._14B

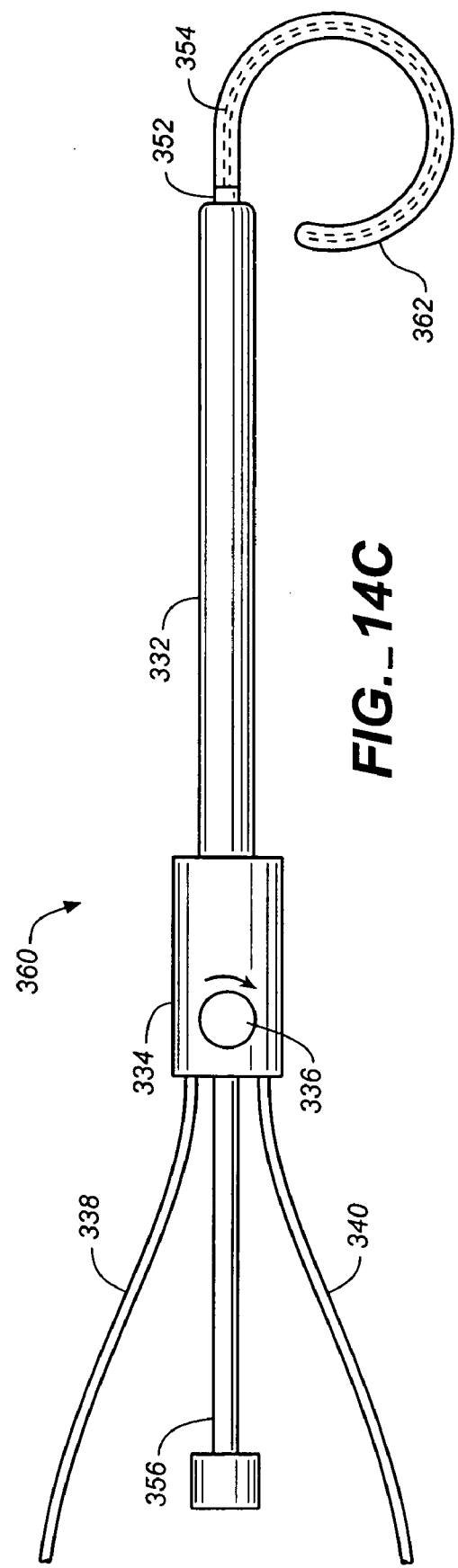

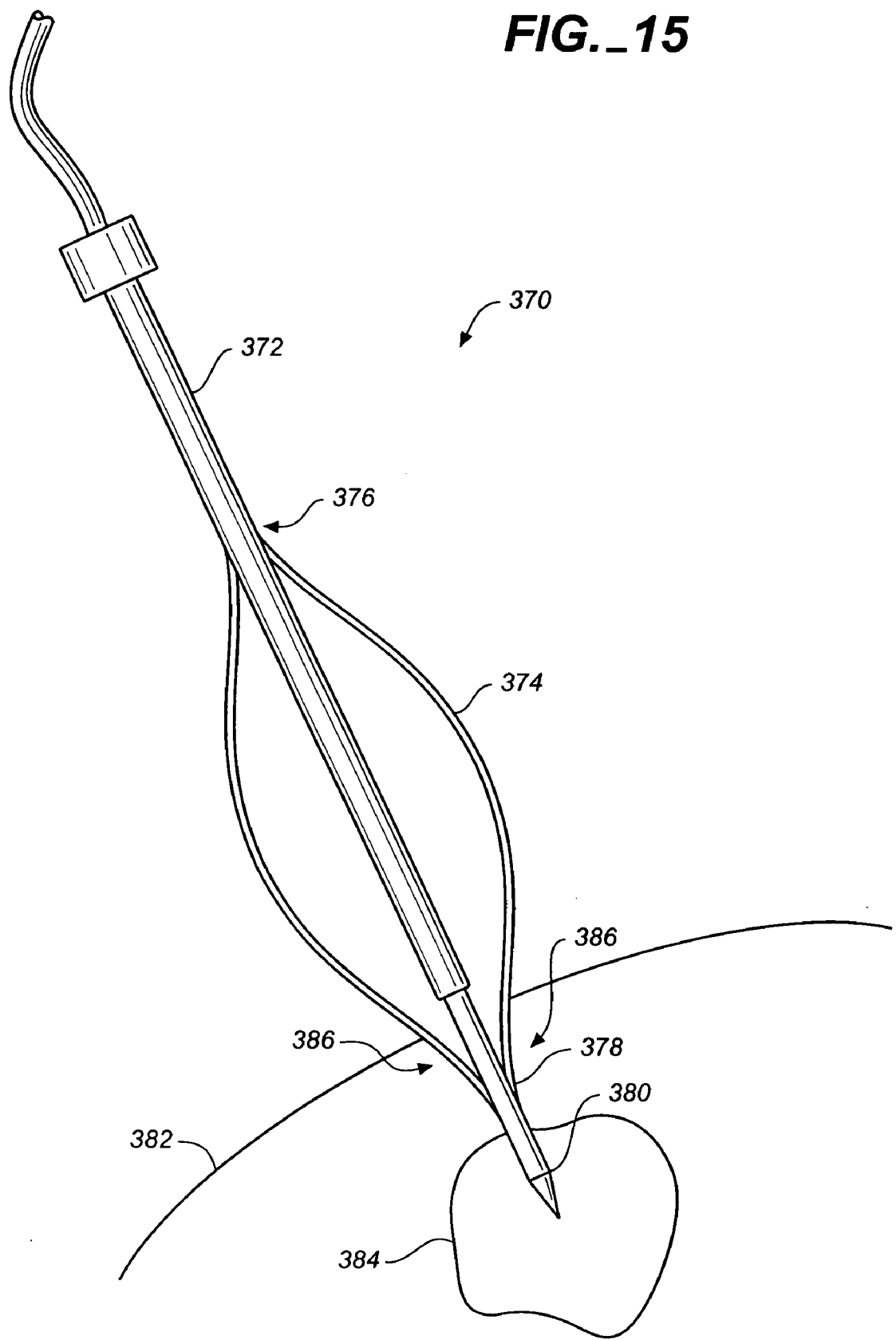
FIG._15

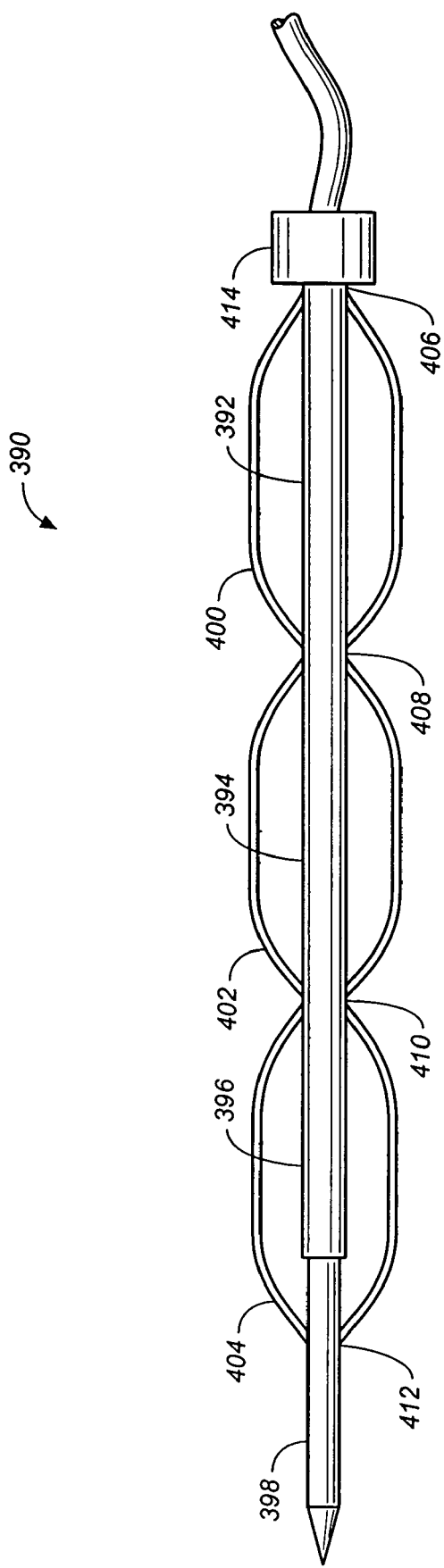
FIG._16

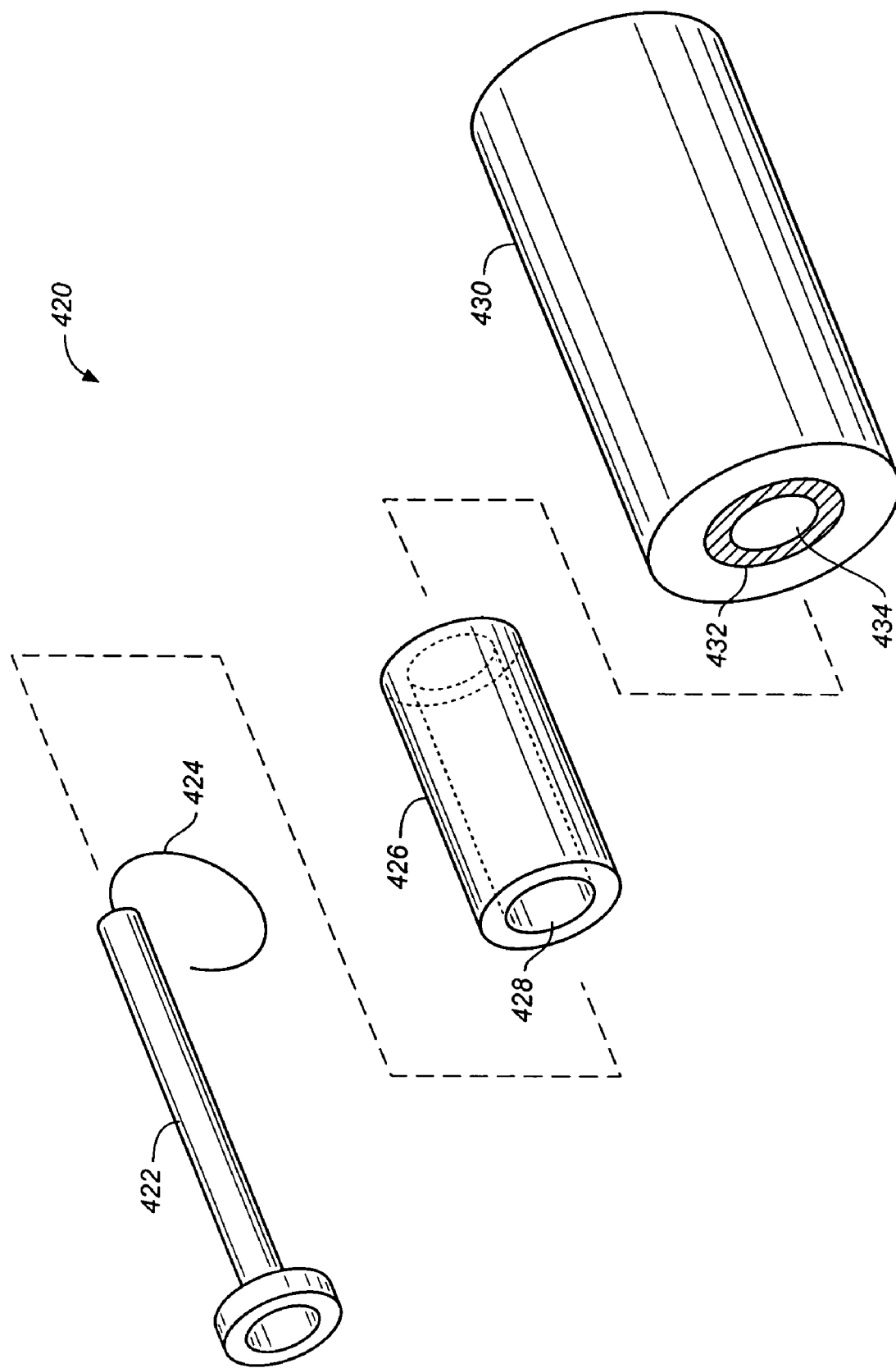
FIG._17

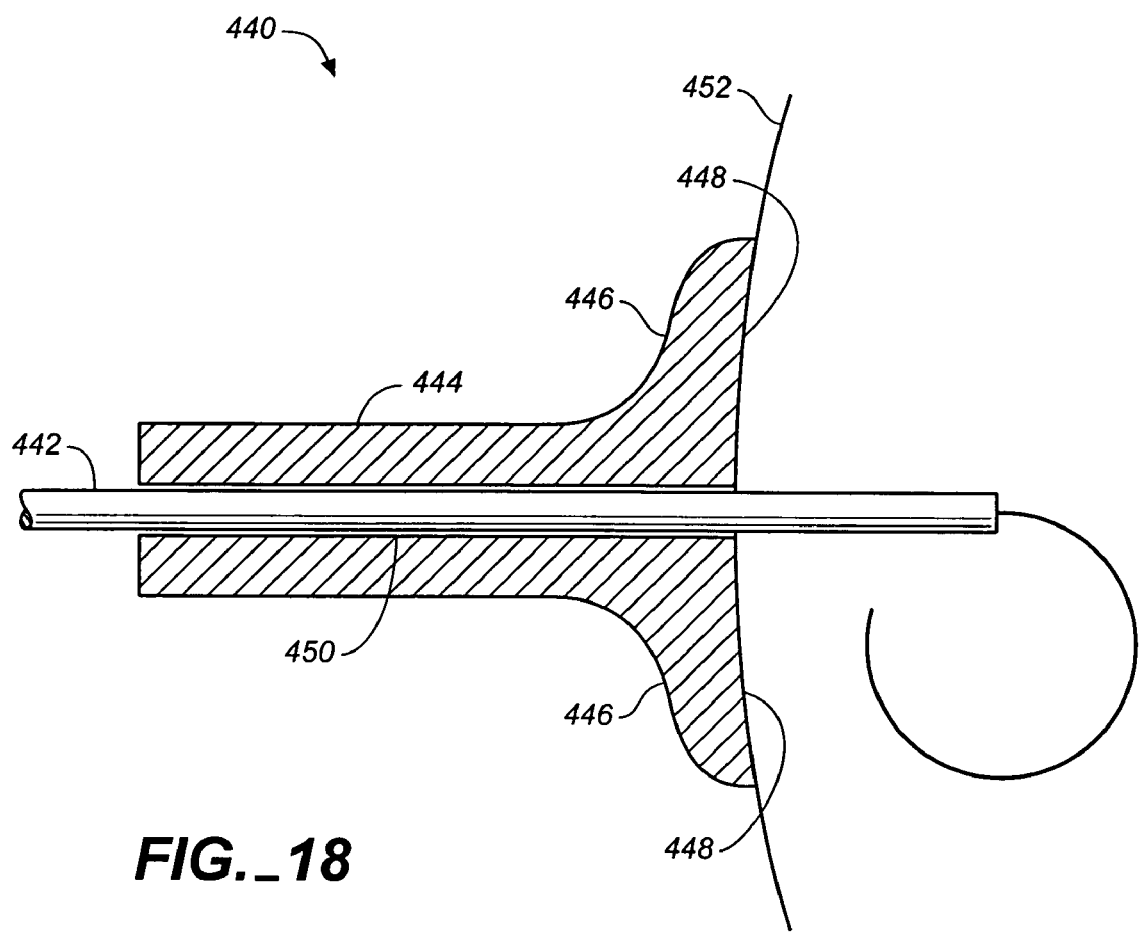
FIG._18

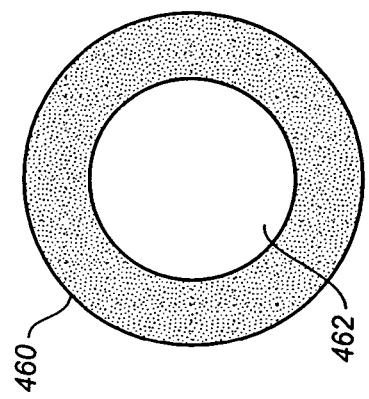
FIG._19B
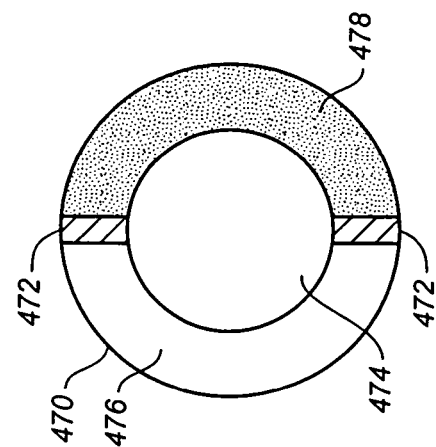
FIG._20B
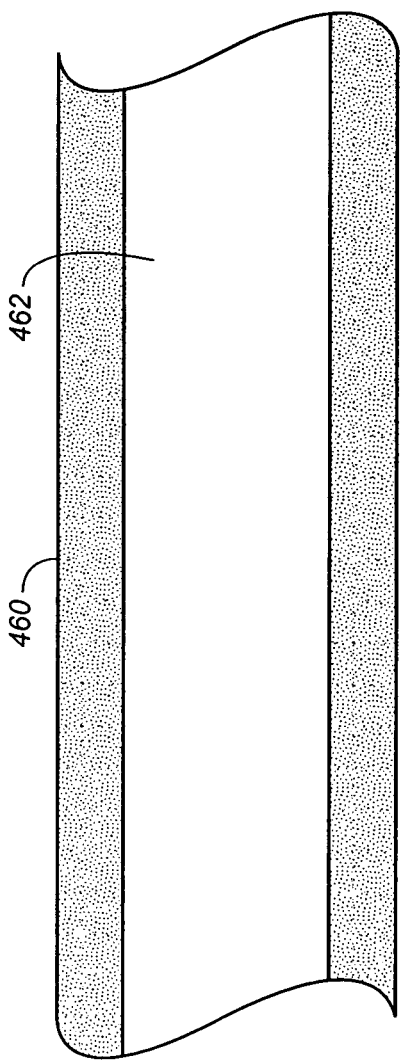
FIG._19A
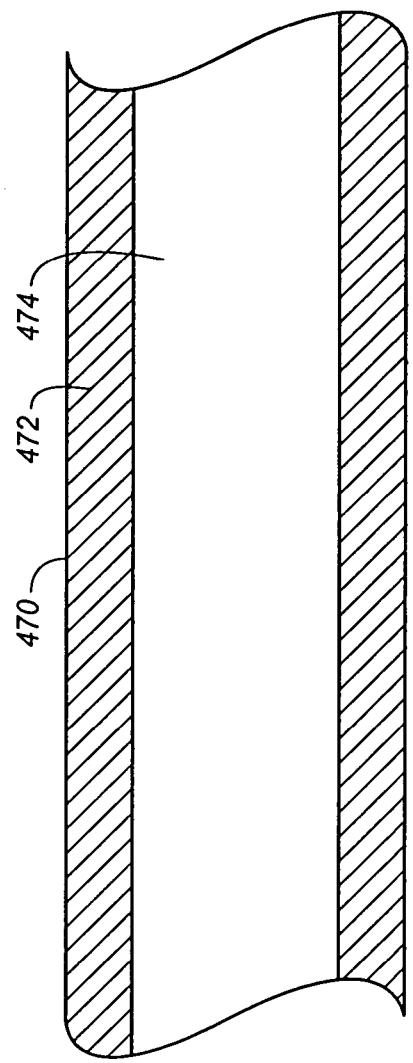
FIG._20A

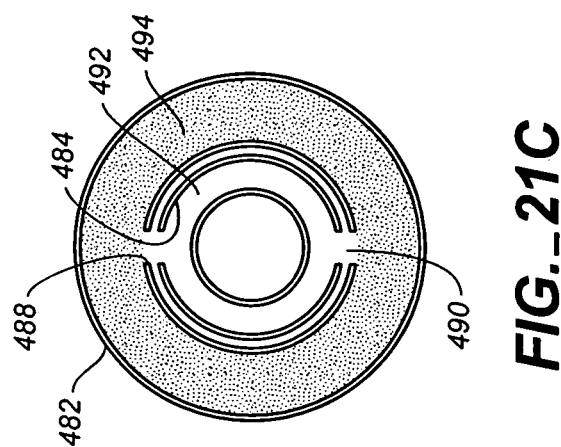
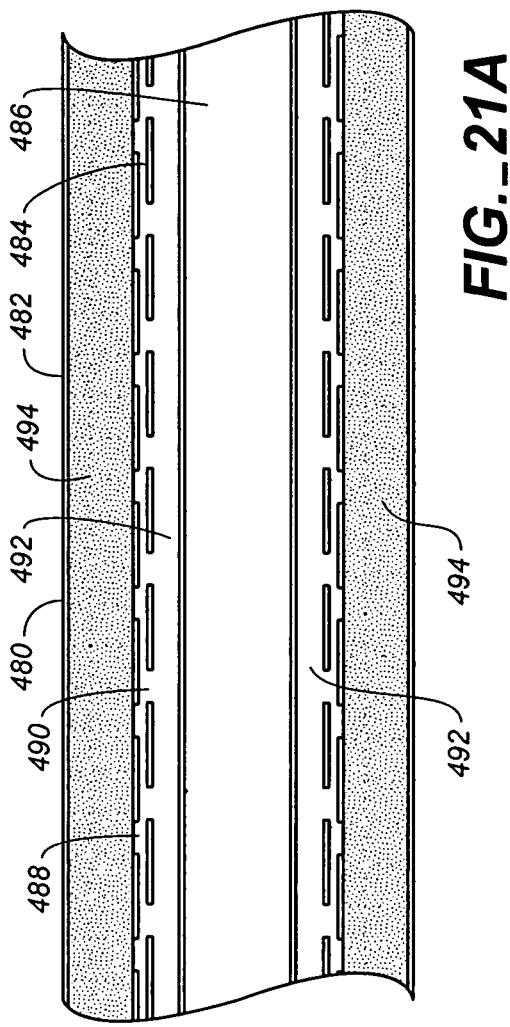
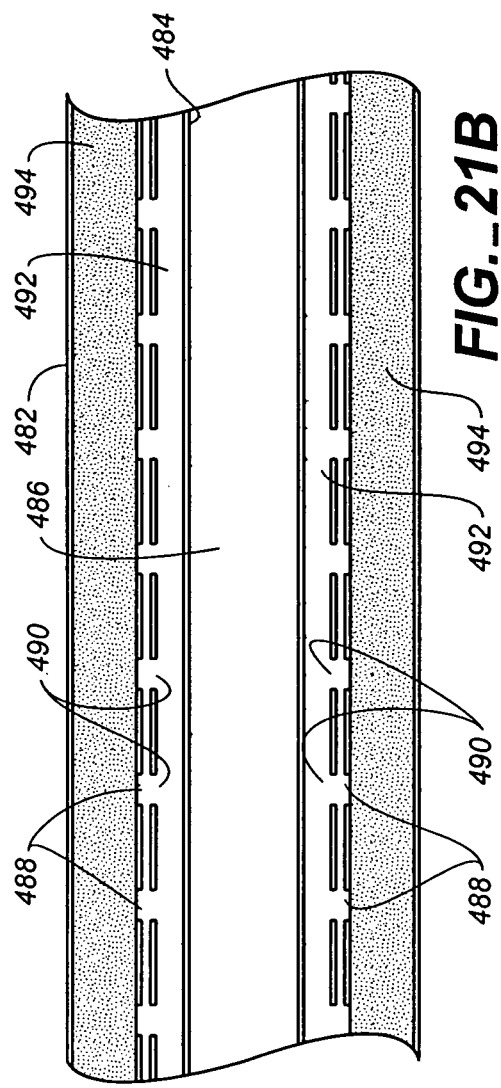

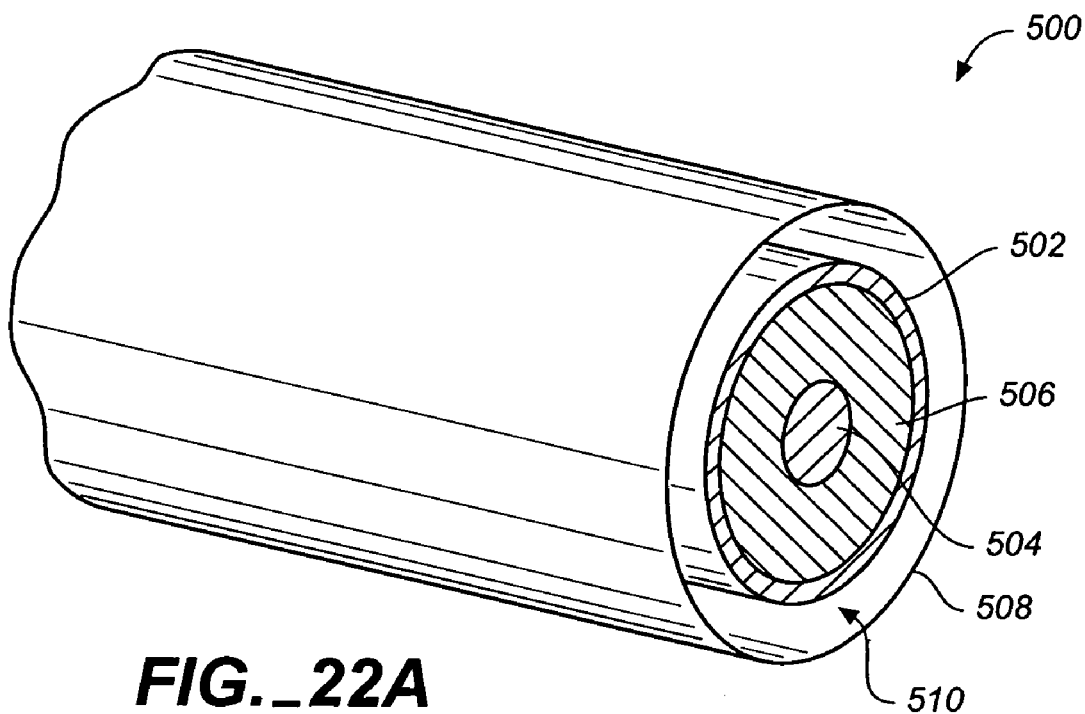
FIG._22A
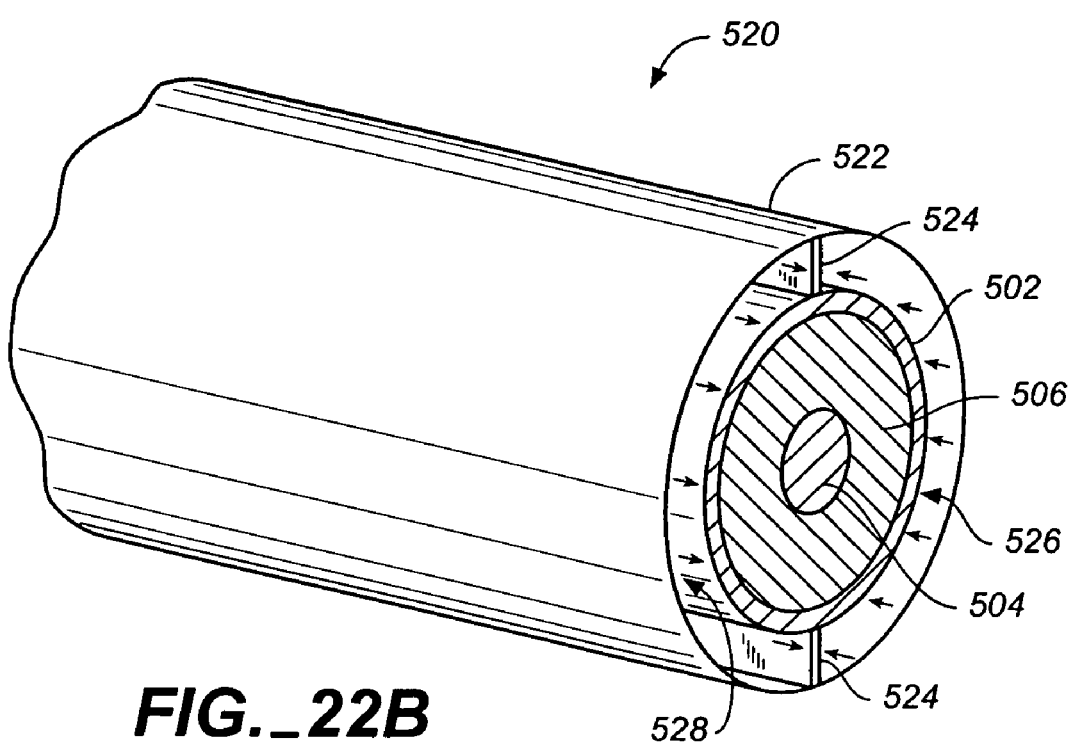
FIG._22B

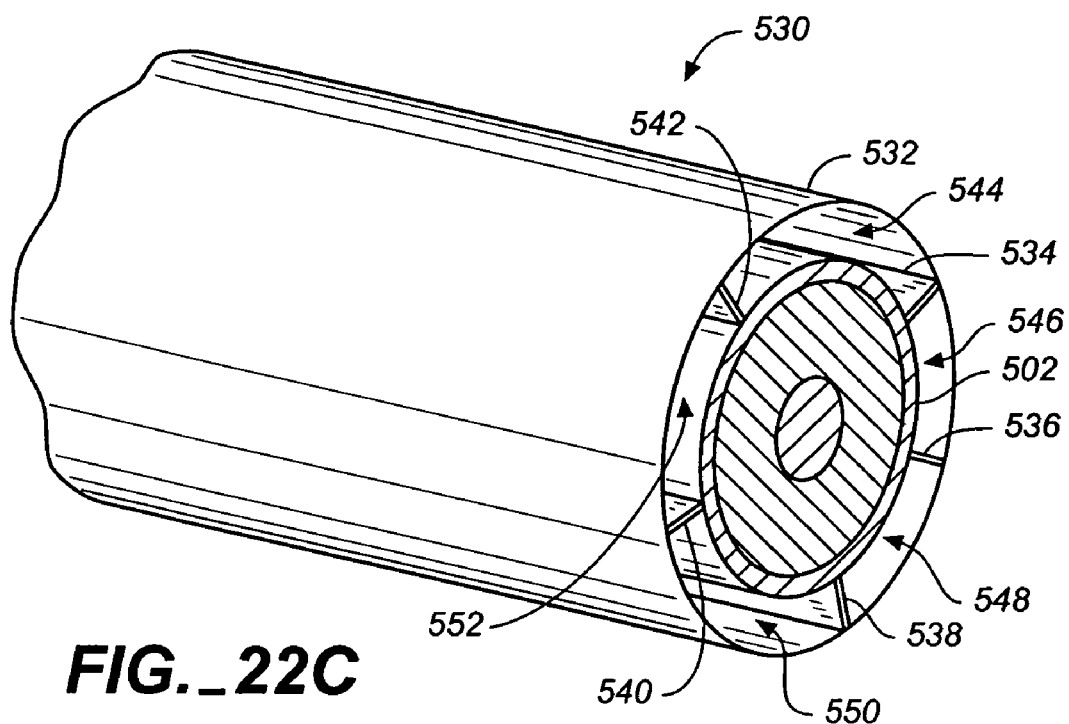
FIG._22C
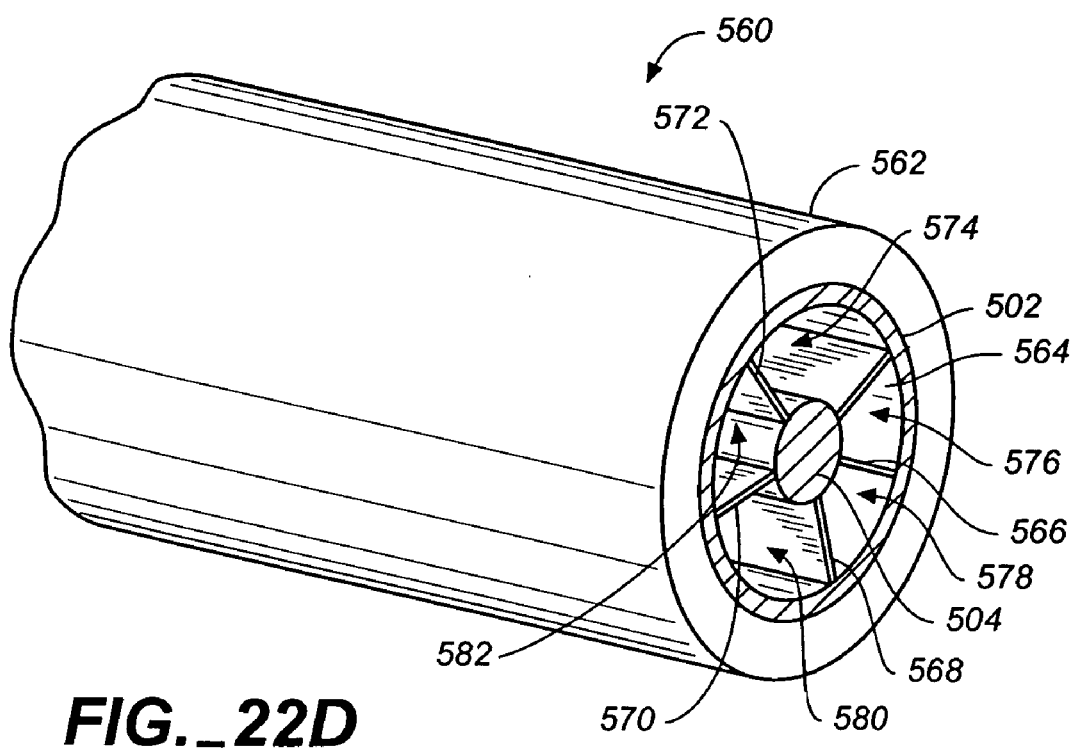
FIG._22D

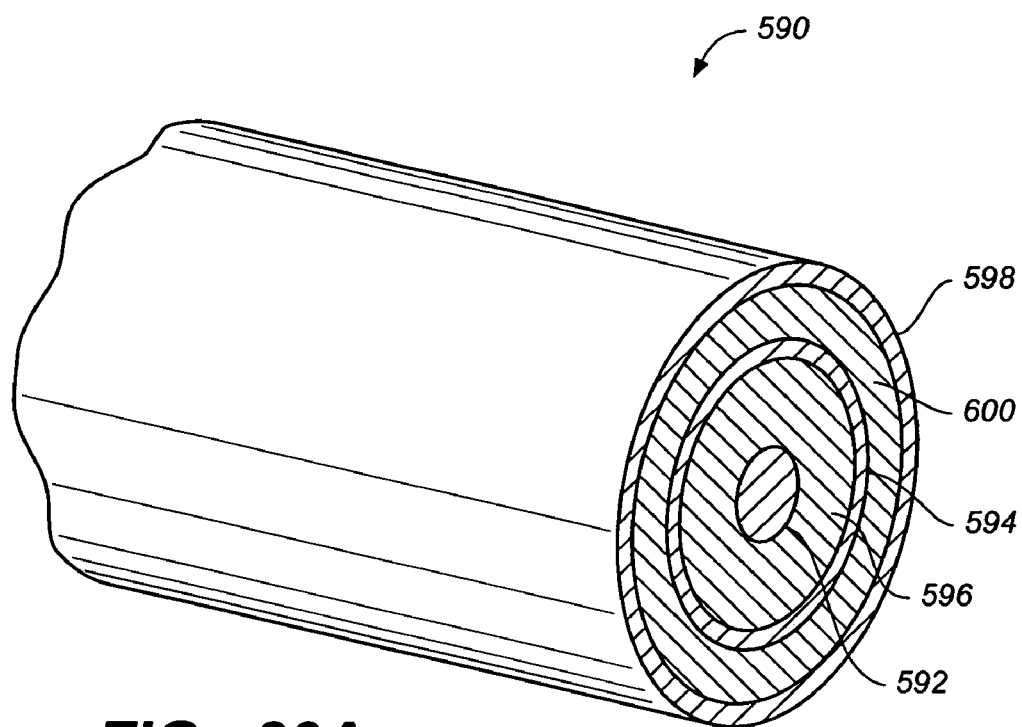
FIG._23A
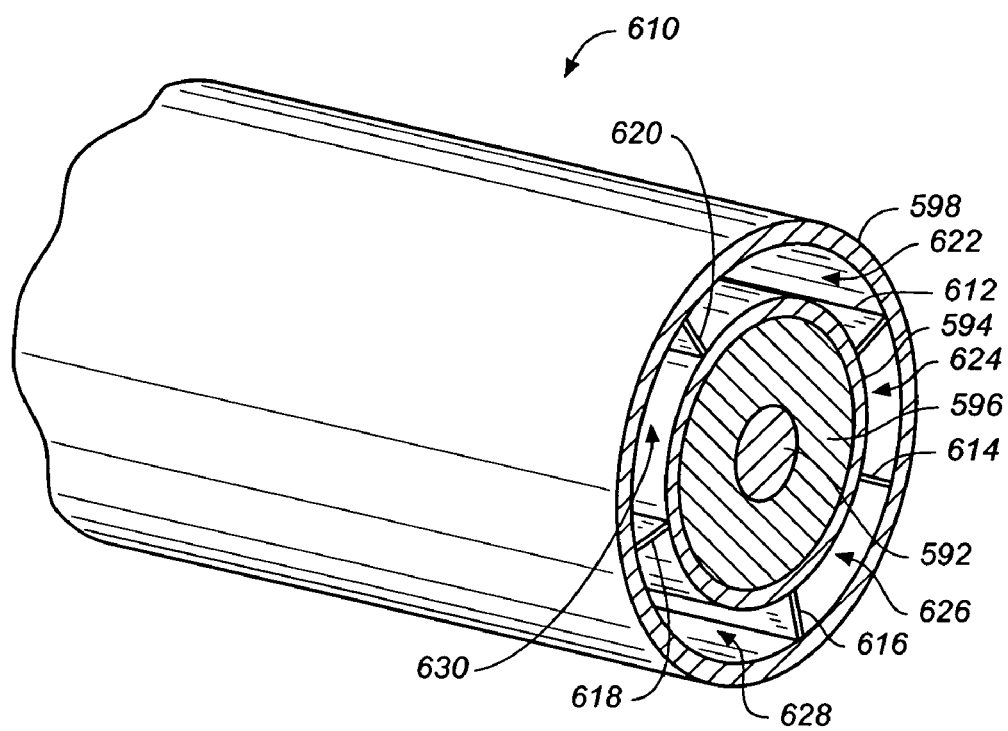
FIG._23B

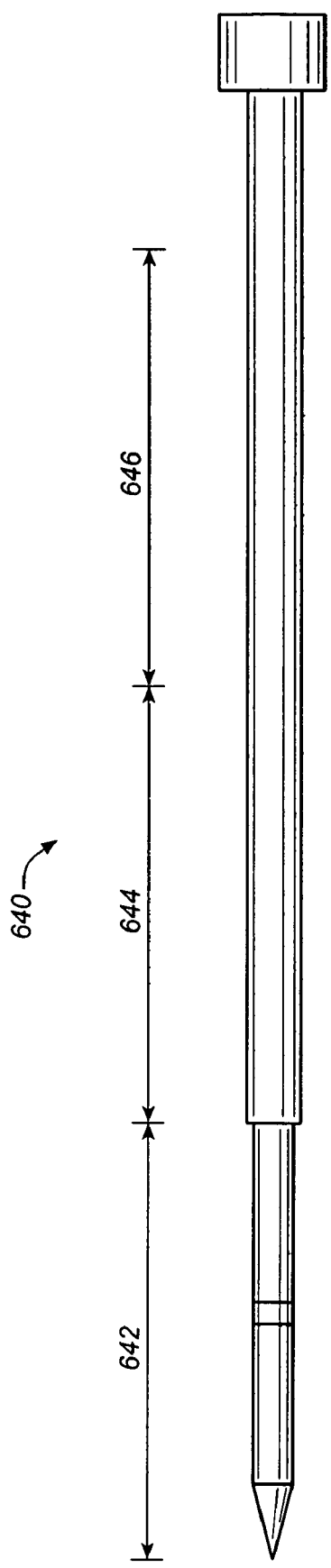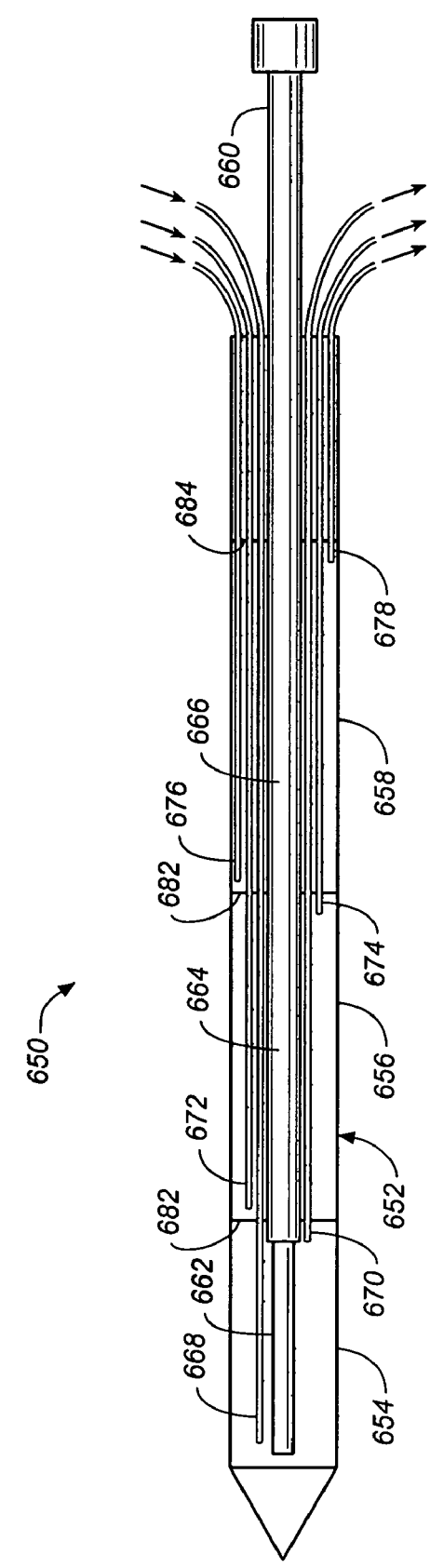

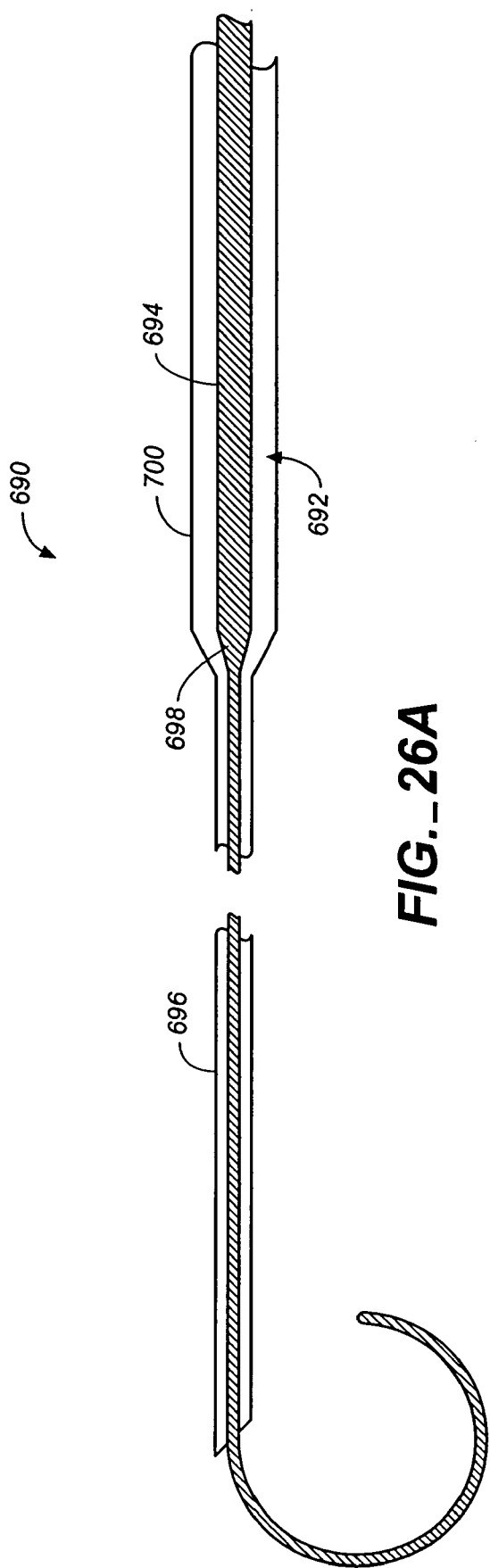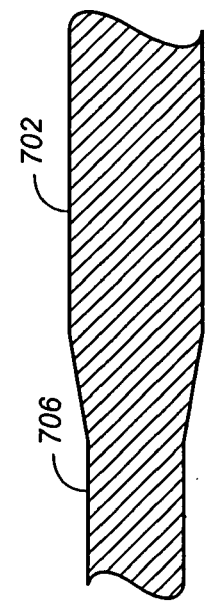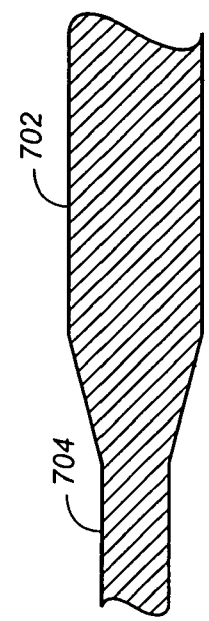

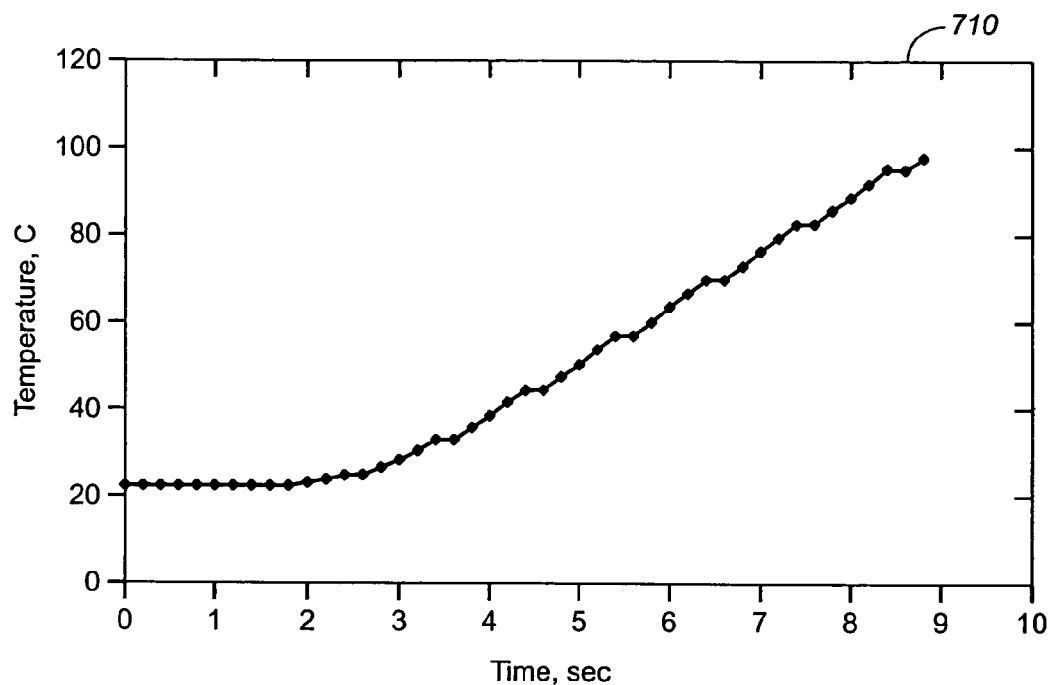
FIG._27
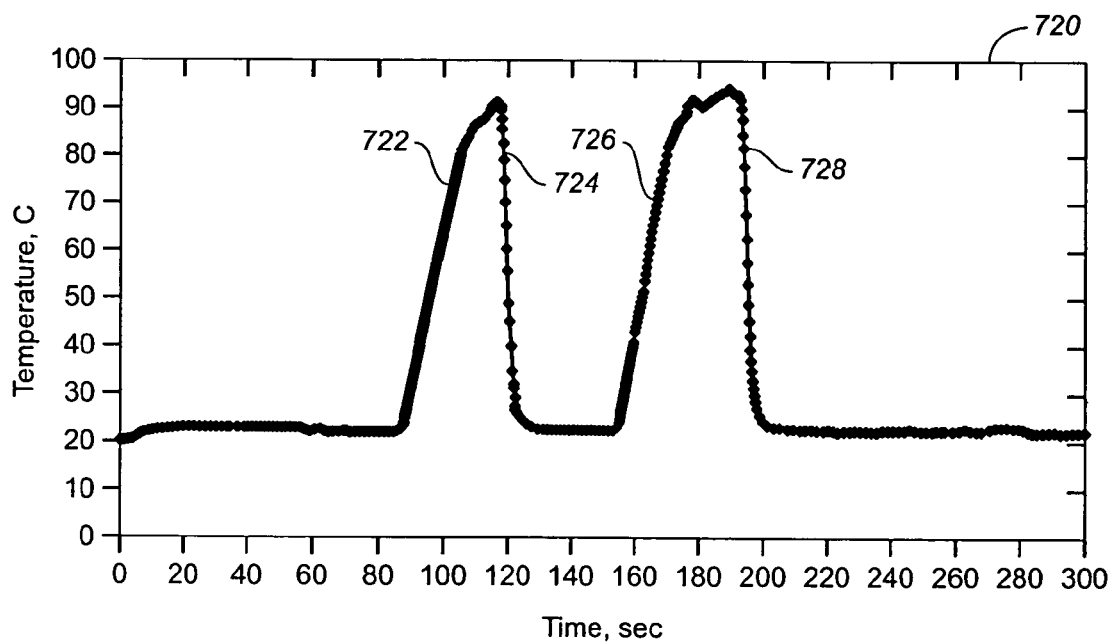
FIG._28

DEVICES AND METHODS FOR COOLING MICROWAVE ANTENNAS

FIELD OF THE INVENTION

The invention relates generally to microwave antennas which may be used in tissue ablation applications. More particularly, the invention relates to devices and methods for reducing or maintaining temperatures of microwave antennas used in such applications.

BACKGROUND OF THE INVENTION

In the treatment of diseases such as cancer, certain types of cancer cells have been found to denature at elevated temperatures which are slightly lower than temperatures normally injurious to healthy cells. These types of treatments, known generally as hyperthermia therapy, typically utilize electromagnetic radiation to heat diseased cells to temperatures above 41° C. while maintaining adjacent healthy cells at lower temperatures where irreversible cell destruction will not occur. Other procedures utilizing electromagnetic radiation to heat tissue also include ablation and coagulation of the tissue. Such microwave ablation procedures, e.g., such as those performed for menorrhagia, are typically done to ablate and coagulate the targeted tissue to denature or kill it. Many procedures and types of devices utilizing electromagnetic radiation therapy are known in the art. Such microwave therapy is typically used in the treatment of tissue and organs such as the prostate, heart, kidney, lung, brain, and liver.

Presently, there are several types of microwave probes in use, e.g., monopole, dipole, and helical, which may be inserted into a patient for the treatment of tumors by heating the tissue for a period of time sufficient to cause cell death and necrosis in the tissue region of interest. Such microwave probes may be advanced into the patient, e.g., laparoscopically or percutaneously, and into or adjacent to the tumor to be treated. The probe is sometimes surrounded by a dielectric sleeve.

However, in transmitting the microwave energy into the tissue, the outer surface of the microwave antennas typically may heat up and unnecessarily necrose healthy tissue immediately adjacent the antenna outer surface. To prevent the charring of adjacent tissue, several different cooling methodologies are conventionally employed. For instance, some microwave antennas utilize balloons which are inflatable around selective portions of the antenna to cool the surrounding tissue. Thus, the complications associated with tissue damaged by the application of microwave radiation to the region is minimized. Typically, the cooling system and the tissue are maintained in contact to ensure adequate cooling of the tissue.

Other devices attempt to limit the heating of tissue adjacent the antenna by selectively blocking the propagation of the microwave field generated by the antenna. These cooling systems also protect surrounding healthy tissues by selectively absorbing microwave radiation and minimize thermal damage to the tissue by absorbing heat energy.

However, in order for microwave ablation to become a truly effective tool for the laparoscopic and/or percutaneous treatment of tumors, an effective microwave antenna should be implemented to efficiently transfer energy to the targeted tissue region while minimizing unnecessary tissue damage adjacent to the antenna outer surface. Moreover, the cooling aspects along the antenna should be controllable to allow for different regions of cooling as well as to allow for the coagulation of adjacent tissue along selected regions of the antenna, if desired.

BRIEF SUMMARY OF THE INVENTION

In minimally invasively treating diseased areas of tissue in a patient, trauma may be caused to the patient resulting in pain and other complications. One cause of trauma may result from excess tissue being unnecessarily ablated by the microwave antenna assembly. As the microwave antenna transmits microwave energy, the feedline or shaft of the antenna may increase in temperature and the contacting tissue may become charred or ablated unnecessarily. Moreover, charred tissue may decrease the effectiveness of the microwave antenna. The cooling systems, as described herein, may be used in conjunction with various types of microwave antennas, e.g., antennas having either a straight or looped radiating antenna portion, etc.

One variation of an antenna cooling system may generally comprise a cooling handle assembly with an elongate outer jacket extending from the handle assembly and terminating at a tip which may be tapered. A microwave antenna may be positioned within the handle assembly and the outer jacket. An inflow tubing may extend into the handle body and distally into at least a portion of the outer jacket. A corresponding outflow tubing may also extend from within handle body such that the distal ends of the inflow tubing and the outflow tubing are in fluid communication with one another. A fluid may be pumped into the handle body via a pump through the inflow tubing such that the fluid comes into contact directly along a portion of the length, or a majority of the length, or the entire length of the antenna to allow for direct convective cooling of the antenna shaft. The fluid may exit the handle body through the outflow tubing. Thus, the cooling assembly is effective in cooling the antenna through direct contact rather than cooling the tissue surrounding the antenna, although the surrounding tissue may also be indirectly cooled through conduction via the assembly.

The cooling fluid used may vary depending upon desired cooling rates and the desired tissue impedance matching properties. Various fluids may be used, e.g., liquids including, but not limited to, water, saline, Fluorinert®, liquid chlorodifluoromethane, etc. In other variations, gases (such as nitrous oxide, nitrogen, carbon dioxide, etc.) may also be utilized as the cooling fluid. In yet another variation, a combination of liquids and/or gases, as mentioned above, may be utilized as the cooling medium.

The distal end of the microwave antenna may be optionally secured within the cooling jacket through various methods. For instance, the antenna may remain either electrically or mechanically unconnected to the cooling assembly tip or the two may be optionally joined via a mechanical connection. In other variations, the antenna and tip may be mechanically and electrically connected, just electrically connected, or just mechanically connected. Various mechanical fastening methods which may be utilized to mechanically connect the antenna and the tip may include, e.g., adhesives, welding, soldering, clamping, crimping, etc.

Other cooling assembly variations may include an outer cooling jacket having an inlet tube externally located from the lumen of the outer jacket. The inlet tube may be a separate tube member attached to the surface of the outer jacket or it may be integrally formed with the outer jacket. Alternatively, an inlet lumen may be defined directly within the wall of the outer jacket. Yet another variation on antenna cooling assembly may include a cooling jacket modified to cover only the radiating portion of the microwave antenna. The cooling jacket may thus be configured to be shortened in length and may further omit a handle portion. Alternatively, another variation may have a cooling tube coiled around at least a portion of the shaft.

Another alternative for cooling a microwave antenna may comprise a passively cooled balloon assembly typically comprising a microwave antenna shaft or feedline with an inflatable balloon over a length of the shaft. The balloon member may be inflatable with a liquid or gas (or combination of both) and attached along the microwave antenna shaft through any variety of attachment methods, e.g., adhesives, crimping, etc. Alternatively, a separate inflatable balloon may simply be placed over the antenna shaft and reside unattached to the microwave antenna. In use, the microwave antenna may be advanced percutaneously or laparoscopically through the skin of a patient to position the antenna radiating portion within, near, or adjacent to a tumor. Once the radiating portion has been desirably positioned within the patient, the balloon may be inflated prior to or during microwave energy transmission through the antenna. The inflation of the balloon may dilate the tissue surrounding the shaft to urge the tissue out of contact with the shaft to prevent the tissue from overheating or becoming charred.

Alternative cooling methods and devices may also comprise passive cooling sheaths generally comprising a tubular cooling pack defining a lumen into which the shaft of the antenna may be positioned. Another variation may comprise a conformable cooling sheath having a proximal handle portion and a conformable portion which may be configured to spread over and cool the skin surface surrounding the area where the antenna shaft has been inserted.

Another alternative may comprise integrated cooling lumens defined through the length of the sheath. Optional barriers may be defined through the length of sheath to divide the interior lumen into at least two separate volumes. Within these lumens, a first defined volume may hold a first chemical or liquid (e.g., water, saline, etc.) and a second defined volume may hold a second chemical or liquid (ammonium chloride, sodium nitrate, or potassium chloride, etc.). When a cooling effect is desired, the sheath may be flexed slightly such that the barriers are broken or fractured within the sheath and allows for the mixing between the chemicals to result in an endothermic reaction. Another alternative may include a slidable sheath assembly comprising an inner tube, which defines a first volume for holding a first chemical or liquid, and a concentric outer tube, which defines a second volume for holding a second chemical or liquid. Alternative variations may have the cooling sheath or tube integrated with or within the microwave antenna shaft.

Cooling sheaths or jackets may be varied or tuned to match the requisite cooling for a given length of a microwave antenna. A typical microwave antenna may generally be divided into at least three different regions along the length of its shaft. For instance, a microwave antenna may be divided into a first region, second region, and third region. Accordingly, a multi-zone cooling assembly may be utilized to take advantage of optionally cooling multiple regions along the length of a microwave antenna.

Finally, yet another variation may include a microwave antenna in which the diameters of the inner conductor are modified so that proximal portions of the inner conductor functions as a heat sink to facilitate conductive cooling of the microwave antenna. This may be accomplished by creating an inner conductor having a larger proximal portion such that the proximal portion functions to draw and dissipate the heat at a faster rate.

BRIEF DESCRIPTION OF THE DRAWINGS

FIG. 1 shows an example of a microwave antenna assembly which may be utilized with the cooling systems described herein.

FIGS. 2A and 2B show representative cross-sectional end and side views, respectively, of a microwave antenna assembly which may be utilized with the cooling systems described herein.

FIG. 3A shows a representative illustration of another variation of a microwave antenna assembly which may be utilized with the cooling systems described herein.

FIG. 3B shows a cross-sectional view of the antenna of FIG. 3A.

FIGS. 4A and 4B show a cross-sectional side view and an end view, respectively, of one variation of an antenna cooling system.

FIG. 4C shows a detail view from FIG. 4A of the cooling system handle.

FIGS. 4D and 4E show detail views from FIG. 4A of alternative cooling configurations for the antenna.

FIG. 5A shows a representative cross-sectional view of the distal end of the antenna within a cooling system.

FIGS. 5B to 5D show cross-sectional side views of alternative attachments between the antenna and cooling system tip.

FIG. 5E shows a cross-sectional side view illustrating one variation in which the cooling system tip may be energized.

FIG. 6 shows a representative side view of another variation of the cooling system which may have an externally positioned fluid tube.

FIG. 7 shows a representative side view of yet another variation of the cooling system which may have an integrated fluid lumen defined within a wall of the outer jacket.

FIG. 8 shows a side view of yet another variation of the cooling system having a separate mandrel for structural support.

FIGS. 9A to 9C illustrate one variation in utilizing the device of FIG. 8.

FIG. 10 shows yet another variation of a cooling system configured to be placed over only the radiating portion of a microwave antenna.

FIG. 11 shows yet another variation of a cooling system comprising a tube which may be coiled over the microwave antenna.

FIGS. 12A and 12B show side and cross-sectional views, respectively, of a loop antenna variation configured to cool the antenna.

FIGS. 13A to 13C show end, cross-sectional side, and perspective views, respectively, of another variation of the system configured as a cooling sheath.

FIG. 14A shows a sheath in one variation used with a straight probe microwave antenna.

FIG. 14B shows the sheath in another variation used with a looped probe microwave antenna.

FIG. 14C shows the sheath in yet another variation used with a looped probe microwave antenna configured to cool the radiating looped antenna portion.

FIG. 15 shows a variation of a straight probe microwave antenna having a dilating balloon used to push surrounding tissue away from the antenna surface.

FIG. 16 shows another variation of a straight probe microwave antenna having multiple dilating balloons positioned along the length of the antenna.

FIG. 17 shows an exploded assembly view of another variation of the cooling system configured as a separate cooling sheath positionable over the microwave antenna shaft.

FIG. 18 shows a side view of yet another variation of a cooling sheath configured to conform at least partially to the tissue surface.

FIGS. 19A and 19B show cross-sectional side and end views, respectively, of a cooling sheath.

FIGS. 20A and 20B show cross-sectional side and end views, respectively, of another variation on the cooling sheath having a divider which may be breached to allow the intermixing of chemicals to create a cooling endothermic reaction.

FIGS. 21A and 21B show cross-sectional side views of yet another variation on the cooling sheath in which slidable concentric tubes have openings which are alignable to allow for the intermixing of chemicals to create a cooling endothermic reaction.

FIG. 21C shows an end view of the cooling sheath of FIG. 21B where the openings are aligned.

FIG. 22A shows a perspective view of one example of a cooling sheath positioned over the microwave antenna.

FIGS. 22B and 22C show perspective views of other variations of cooling sheaths having a number of fluid lumens defined between the sheath and antenna surface.

FIG. 22D shows a perspective view of another variation in which the dielectric between the inner and outer conductors may define a number of cooling lumens therethrough.

FIG. 23A shows a perspective view of a portion of a triaxial microwave antenna shaft.

FIG. 23B shows an example of cooling lumens which may be defined through the dielectric between the outer conductor and the choke layer.

FIG. 24 shows a side view of a straight microwave antenna probe delineating the various regions along the antenna shaft which may be in contact with various regions of tissue.

FIG. 25 shows yet another variation of a cooling system which may be configured to delineate multiple regions of varied cooling along the shaft of the microwave antenna.

FIG. 26A shows yet another variation in which a diameter of the coaxial cable may be non-uniform such that a larger cable may have improved power handling capabilities which facilitate a decrease in the generation of high temperatures.

FIGS. 26B and 26C show cross-sectional side views of other transitional diameters for the inner conductor of FIG. 26A.

FIG. 27 shows a plot illustrating the temperature rise over time of an uncooled microwave antenna.

FIG. 28 shows a plot illustrating the decrease in microwave antenna temperature when the cooling system is activated.

DETAILED DESCRIPTION OF THE INVENTION

Various microwave antenna assemblies and cooling systems, as described herein, are less traumatic than devices currently available and as described in further detail below. Generally, in invasively treating diseased areas of tissue in a patient, trauma may be caused to the patient resulting in pain and other complications. One cause of trauma may result from excess tissue being unnecessarily ablated by the microwave antenna assembly. As the microwave antenna transmits microwave energy, the feedline or shaft of the antenna, as well as the radiation portion, may increase in temperature due to ohmic heating. Tissue in contact with a surface of the antenna may thus become charred or ablated unnecessarily. Aside from unnecessary trauma, charred tissue may decrease the effectiveness of the microwave antenna because of the changing impedance of the tissue as it dries out and becomes charred. The cooling systems, as described herein, may be used in conjunction with various types of microwave antennas.

Examples of various types of microwave antenna assemblies which may be used with the cooling systems herein shall now be described. For instance, FIG. 1 shows a representative diagram of a variation of a microwave antenna assembly 10 which may be used with a cooling system as described herein. The antenna assembly 10 is generally comprised of radiating portion 12 which may be connected by feedline 14 (or shaft) via cable 16 to connector 18, which may further connect the assembly 10 to a power generating source 30, e.g., a generator. Assembly 10, as shown, is a dipole microwave antenna assembly, but other antenna assemblies, e.g., monopole or leaky wave antenna assemblies, may also be utilized. Distal portion 22 of radiating portion 12 preferably has a tapered end 26 which terminates at a tip 28 to allow for insertion into tissue with minimal resistance. In those cases where the radiating portion 12 is inserted into a pre-existing opening, tip 28 may be rounded or flat.

Generally, the antenna assembly 10 in FIG. 1 shows a variation where a compressive load may be used to increase antenna strength. Proximal portion 24 is located proximally of distal portion 22, and junction member 20 is preferably located between both portions such that a compressive force is applied by distal and proximal portions 22, 24 upon junction member 20. Placing distal and proximal portions 22, 24 in a pre-stressed condition prior to insertion into tissue enables assembly 10 to maintain a stiffness that is sufficient to allow for unaided insertion into the tissue while maintaining a minimal antenna diameter, as described in detail below.

Feedline 14 may electrically connect antenna assembly 10 via cable 16 to generator 30 and usually comprises a coaxial cable made of a conductive metal which may be semi-rigid or flexible. Feedline 14 may also have a variable length from a proximal end of radiating portion 12 to a distal end of cable 16 ranging between about 1 to 15 inches. Most feedlines may be constructed of copper, gold, or other conductive metals with similar conductivity values, but feedline 14 is preferably made of stainless steel. The metals may also be plated with other materials, e.g., other conductive materials, to improve their properties, e.g., to improve conductivity or decrease energy loss, etc. A feedline 14, such as one made of stainless steel, preferably has an impedance of about 50 Ω and to improve its conductivity, the stainless steel may be coated with a layer of a conductive material such as copper or gold. Although stainless steel may not offer the same conductivity as other metals, it does offer strength required to puncture tissue and/or skin.

FIGS. 2A and 2B show an end view and a cross-sectional view, respectively, of a conventional dipole microwave antenna assembly 40 which may be utilized with the cooling systems described herein. As seen, antenna assembly 40 has a proximal end 42 which may be connected to a feedline 14 and terminates at distal end 44. The radiating portion of antenna 40 comprises proximal radiating portion 46 and distal radiating portion 48. Proximal radiating portion 46 may typically have an outer conductor 52 and an inner conductor 54, each of which extends along a longitudinal axis. Between the outer and inner conductors 52, 54 is typically a dielectric material 56 which is also disposed longitudinally between the conductors 52, 54 to electrically separate them. A dielectric material may constitute any number of appropriate materials, including air. Distal portion 58 is also made from a conductive material, as discussed below. Proximal and distal radiating portions 46, 48 align at junction 50, which is typically made of a dielectric material, e.g., adhesives, and are also supported by inner conductor 54 which runs through junction opening 60 and at least partially through distal portion 58. However, as discussed above, the construction of conventional antenna assembly 40 is structurally weak at junction 50.

A further detailed discussion of microwave antennas which may be utilized herein may be found in U.S. patent application Ser. No. 10/052,848 entitled "High-Strength Microwave Antenna Assemblies" filed Nov. 2, 2001 and U.S. patent application Ser. No. 10/272,058 entitled "High-Strength Microwave Antenna Assemblies And Methods Of Use" filed Oct. 15, 2002, each of which is incorporated herein by reference in its entirety.

An alternative microwave antenna having a curved microwave antenna may also be utilized with the cooling systems described herein as shown in FIG. 3A. Microwave antenna assembly 70 may comprise at least one microwave antenna 72 electrically connected to generator 82. Microwave antenna 72 preferably comprises shaft or feedline 74 with a distal end from which antenna or inner conductor 76 extends to define the ablation region 90. The proximal end of feedline 74 preferably comprises coupler 78 which electrically couples the antenna 72 to generator 82 via power transmission cable 80. The cable 80 is preferably a flexible cable which allows for the positioning of antenna 72 relative to a patient.

Feedline 74 is preferably a coaxial cable, as shown by the cross-section 3B-3B in FIG. 3B taken from FIG. 3A. The feedline 74, similar to feedline 14 described above, may be formed of outer conductor 84 surrounding inner conductor 86. Conductors 84, 86 may be made of a conductive metal which may be semi-rigid or flexible. Most feedlines 84, as described above, may be constructed of metals such as stainless steel. Alternatively, metals such as copper, gold, or other conductive metals with similar conductivity values may also be utilized. A dielectric material 88 is preferably disposed between outer and inner conductors 84, 86, respectively, to provide insulation therebetween and may be comprised of any appropriate variety of conventional dielectric materials.

Additional details regarding the curved loop microwave antenna configuration which may be utilized herein are further described in U.S. patent application Ser. No. 10/272,314 entitled "Microwave Antenna Having A Curved Configuration" filed Oct. 15, 2002, which is incorporated herein by reference in its entirety.

FIGS. 4A and 4B show a cross-sectional side view and an end view, respectively, of one variation of an antenna cooling system which may be utilized with any number of conventional microwave antennas or the microwave antennas described herein, particularly the straight probe configuration as shown in FIGS. 1 and 2A-2B. Although this variation illustrates the cooling of a straight probe antenna, a curved or looped microwave antenna may also utilize much of the same or similar principles, as further described below. Antenna cooling assembly 100 may generally comprise a cooling handle assembly 102 and an elongate outer jacket 108 extending from handle assembly 102. Outer jacket 108 may extend and terminate at tip 110, which may be tapered to a sharpened point to facilitate insertion into and manipulation within tissue, if necessary. Microwave antenna 104 may be positioned within handle assembly 102 such that the radiating portion 106 of antenna 104 extends distally into outer jacket 108 towards tip 110. Inflow tubing 114 may extend into a proximal end of handle body 112 and distally into a portion of outer jacket 108. Outflow tubing 116 may also extend from within handle body 112 such that the distal ends of inflow tubing 114 and outflow tubing 116 are in fluid communication with one another, as described in further detail below.

FIG. 4C shows handle assembly detail 118 from FIG. 4A. As shown, handle body 112 may be comprised of proximal handle hub 122, which encloses a proximal end of antenna 104, and distal handle hub 124, which may extend distally into outer jacket 108. Proximal handle hub 122 and distal handle hub 124 may each be configured to physically interfit with one another at hub interface 130 to preferably form a fluid tight seal. Accordingly, proximal handle hub 122 may be configured to be received and secured within a correspondingly configured distal handle hub 124, seen in the figure as a male-female connection. Proximal and distal handle hubs 122, 124 may each be formed from the same (or similar) or different materials. If hubs 122, 124 are fabricated from the same material, a variety of non-conductive materials are preferably utilized, e.g., polymers, polyimides, plastics, etc. Alternatively, proximal handle hub 122 may be fabricated from a metal or alloy, e.g., stainless steel, platinum, nickel, nickel-titanium, etc., while distal handle hub 124 (or just the handle portion over the radiating portion of the microwave antenna) may be fabricated from one of the non-conductive materials previously mentioned.

The distal ends of inflow tubing 114 and outflow tubing 116 may be positioned within handle body 112 such that fluid may be pumped into handle body 112 via a pump (not shown) through inflow tubing 114. Fluid entering handle body 112 may come into direct contact with at least a portion of the shaft of antenna 104 to allow for convective cooling of the antenna shaft to occur. The fluid may be allowed to exit handle body 112 via outflow tubing 116. An additional inlet tube 126 may be positioned within antenna cooling assembly 100 to extend between handle body 112 and radiating portion 106 of antenna 104 and a corresponding outlet tube 128 may also extend between handle body 112 and radiating portion 106. The proximal end of inlet tube 126 may be in fluid communication with inflow tubing 114 to allow the cooling fluid to flow distally within outer jacket 108 towards antenna radiation portion 106. Alternatively, inlet tube 126 and outlet tube 128 may be omitted from cooling assembly 100 and outer jacket 108 may remain in direct fluid communication with inflow tubing 114 and outflow tubing 116 such that fluid contacts the antenna 104 directly along a portion of the length, or a majority of the length, or the entire length of antenna 104. Thus, the cooling assembly 100 is effective in cooling the antenna 104 directly rather than cooling the tissue surrounding the antenna 104, although the surrounding tissue may also be conductively cooled via assembly 100.

FIGS. 4D and 4E shows outer jacket detail variations 120, 120', respectively, from FIG. 4A. FIG. 4D shows one variation where the distal end 132 of inlet tube 126 may extend distally through outer jacket 108. The opening at distal end 132 may be positioned within outer jacket 108 near or at the distal end of outer jacket 108 such that distal end 132 opens to fluid channel 134. The cooling fluid may enter fluid channel 134 and fill the volume surrounding at least a portion of the antenna 104, and preferably surrounding at least the radiation portion 106. As fluid enters fluid channel 134, it may be withdrawn through a distal opening in outlet tube 128, which is preferably located proximally of distal end 132 to allow for increased convective cooling between the cooling fluid and the antenna 104. Alternatively, each of the distal ends of inlet tube 126 and outlet tube 128 may be aligned with one another. In either case, the cooling fluid may directly contact the outer surface of the antenna 104 and envelope the antenna 104 rather than being in conductive contact through some additional thermal interface. Allowing the direct fluid-to-antenna contact enables direct convective cooling to occur and may thereby facilitate the heat transfer from the antenna to the cooling fluid.

The cooling fluid may be pumped using positive pressure through inlet tube 126; alternatively, negative pressure may also be used to draw the fluid out of the region through outlet tube 128. Negative pressure through outlet tube 128 may be utilized either alone or in conjunction with positive pressure through inlet tube 126. Alternatively, positive pressure through inlet tube 126 may be utilized either alone or in conjunction with negative pressure through outlet tube 128. In pumping the cooling fluid through cooling assembly 100, the cooling fluid may be passed through assembly 100 at a constant and uniform flow rate. In another variation, the flow may be intermittent such that a volume of cooling fluid may be pumped into fluid channel 134 and allowed to warm up by absorbing heat from the antenna. Once the temperature of the fluid reaches a predetermined level below temperatures where thermal damage to tissue occurs, e.g., about 43° to 45° C., the warmed fluid may be removed and displaced by additional cooling fluids. Temperature sensors (such as thermistors, thermocouples, etc.) may be incorporated within or upon the outer jacket 108 to sense the fluid and/or outer jacket 108 temperatures. The system may be configured to automatically pump additional cooling fluid into cooling assembly 100 once the sensed temperature reaches the predetermined level or it may be configured to notify the user via, e.g., an audible or visual alarm.

The cooling fluid used may vary depending upon desired cooling rates and the desired tissue impedance matching properties. Preferably, biocompatible fluids having sufficient specific heat values for absorbing heat generated by microwave ablation antennas may be utilized, e.g., liquids including, but not limited to, water, saline, Fluorinert®, liquid chlorodifluoromethane, etc. In another variation, gases (such as nitrous oxide, nitrogen, carbon dioxide, etc.) may also be utilized as the cooling fluid. For instance, an aperture may be configured at the opening of distal end 132 to take advantage of the cooling effects from the Joule-Thompson effect, in which case a gas, e.g., nitrous oxide, may be passed through the aperture to expand and cool the enclosed antenna 104. In yet another variation, a combination of liquids and/or gases, as mentioned above, may be utilized as the cooling medium.

FIG. 4E shows another variation in detail 120' within outer jacket 108 which incorporates a barrier or gasket 138 to separate the radiating portion 142 of antenna 106 from a proximal portion of the antenna shaft. Barrier 138 may be, e.g., a polymeric or rubber material, configured to function as a gasket to maintain a fluid tight seal around the shaft of the antenna 106. Fluid channel 140 may be defined within outer jacket 108 distally of barrier 138 within which radiating portion 142 may be positioned. A fluid, such as any one of the fluids mentioned above, may be maintained statically within fluid channel 140 to absorb heat generated by radiating portion 142. Alternatively, channel 140 may be filled with a fluid, high-temperature chemical, e.g., epoxy, for better impedance matching with the antenna 106. A separate fluid channel may be defined proximally of barrier 138 surrounding the remaining shaft portion of the antenna. An inlet tube 136 may be positioned within this proximal channel to allow for the exchange of cooling fluids therewithin in a manner as described above such that the fluid is allowed to directly contact the antenna shaft surface.

The distal end of the microwave antenna may optionally be secured within the cooling jacket through a variety of methods. FIG. 5A shows an illustrative cross-sectional view of cooling assembly distal end 150 which shows microwave antenna 154 positioned within outer jacket 152. Although antenna 154 may remain either electrically or mechanically unconnected to cooling assembly tip 156, the two may optionally be joined via a connection 158. FIG. 5B shows one variation of connecting antenna 154 to tip 156 in which they may be mechanically and electrically connected. Tip 156 may be fabricated from a metal or alloy, e.g., stainless steel, and define a contact channel at its proximal end for receiving antenna 160, which may also be metallic. Antenna end 160 may be secured into an electrically conductive connection 162 with tip 156 through various mechanical fastening methods, e.g., adhesives, welding, soldering, clamping, crimping, press-fit, etc., such that connection 162 is a mechanical joint sufficiently strong enough to resist failure when deployed into tissue while also providing for an electrical connection.

FIG. 5C shows another variation where antenna 164 may be mechanically connected to but electrically insulated from tip 156. Antenna 164, or at least the portion of antenna 164 in contact with tip 156, may have an insulative layer 166 over its outer surface. Thus, tip 156 may remain electrically insulated from antenna 164 yet retain the structural connection therebetween, as described above. In yet another alternative, FIG. 5D shows a connection in which antenna 154 may be electrically connected to tip 156 via a wire or cable 168. Such a connection may be used to provide for electrical communication between antenna 154 and tip 156 but does not provide for structural support between the two.

In the case where antenna 164 is structurally attached to tip 156 yet electrically insulated, as shown in FIG. 5C, FIG. 5E shows a variation where electrical communication with tip 156 may be maintained with an externally located power source 161 to provide power for energizing tip 156. Energized tip assembly 151 shows antenna 164 structurally connected to tip 156 with insulative layer 166 positioned therebetween. Antenna 164 is shown positioned within outer jacket 153. Rather than having a direct electrical connection between wire 159 and tip 156, wire 159 may be connected to choke 155 such that power source 161 is electrically connected to tip 156 through choke 155, in an alternative variation. In yet another variation, power source 161 may instead be electrically connected to tip 156 via outer conductor 157 through wire 159. In the variations where wire 159 is connected to either choke 155 or outer conductor 157, an electrical connection between antenna 164 and tip 156 is present.

Rather than utilizing separate inlet and outlet tubes, other variations may also be utilized. FIG. 6 shows a side view of another cooling assembly variation 170. In this variation, outer jacket 172 may have an inlet tube 176 externally located from the lumen of outer jacket 172. Tube 176 may be fabricated from the same or similar material as outer jacket 172, as described above, or it may be made from a material different from outer jacket 172, provided that it is preferably non-electrically conductive. Tube 176 may be a completely separate tube member attached to the surface of outer jacket 172. Alternatively, tube 176 may be integrally formed with outer jacket 172. In either case, cooling fluid may be pumped through tube 176 to flow distally along outer jacket 172, as shown by the arrows, until it passes through opening 180, which may allow for the fluid communication between tube 176 and outlet channel 178 defined through the interior of outer jacket 172. Opening 180 may be defined between tube 176 and outlet channel 178 at a predetermined location along outer jacket 172 proximal to tip 174. The location of opening 180 may depend upon the desired cooling effects and the desired location along the antenna over which the cooling fluid may flow. In another variation, the cooling fluid may be pumped into cooling jacket 172 through outlet channel 178 and the discharged fluid may be returned through tube 176.

FIG. 7 shows a side view of another cooling assembly variation 190. Outer jacket 192 may be seen with tip 194 at its terminal end. In this variation, however, inlet lumen 196 may be defined directly within the wall of outer jacket 192. Inlet lumen 196 may terminate at opening 200 which may be in fluid communication with outlet channel 198, within which a microwave antenna may be situated. Although opening 200 is shown terminating at the distal end of outer jacket 192, opening 200 may be defined at some predetermined location along outer jacket 192 proximal to tip 194 between inlet lumen 196 and outlet channel 198. Furthermore, outer jacket 192 may be fabricated out of any one of the materials as described above.

A combination introducer and cooling sheath is shown in the side view of assembly 210 in FIG. 8. Cooling introducer assembly 210 may comprise a polymeric tubing 212 having tubing hub 214 located at the proximal end of tubing 212. Tip 216, which may be tapered to facilitate assembly 210 introduction into tissue, may be located at the distal end of tubing 212. A removable elongate mandrel 218 may be inserted within tubing 212 to provide structural support and column strength to tubing 212 during insertion of assembly 210 into tissue. Mandrel 218 may be fabricated from various materials having sufficient strength to withstand bending moments generated by tubing 212 during tissue insertion, e.g., stainless steel, and may be configured to slidably fit within lumen 220.

FIGS. 9A to 9C show one example of how assembly 210 may be used as an introducer and cooling jacket for the ablative treatment of tissue. Tubing 212, with mandrel 218 positioned within, may be inserted into the tissue of a patient 230 until a distal portion of tubing 212 is positioned adjacent to or within a diseased region of tissue, e.g., tumor 232, as shown in FIG. 9A. Once tubing 212 has been desirably positioned, inner mandrel 218 may be removed from tubing 212 while maintaining the position and orientation of tubing 212 within patient 230, as shown in FIG. 9B. Microwave antenna 236 may then be inserted within lumen 220 of tubing 212 and advanced distally therewithin such that radiating portion 238 of antenna 236 is positioned within the distal portion of tubing 212 which is adjacent to or within tumor 232. The proximal end of antenna 236 may have cooling hub 234 connected thereto and cable 240 extending proximally for connection to a microwave and/or RF power supply (not shown).

The length of antenna 236 may be configured to fit within tubing 212 such that tubing hub 214 and cooling hub 234 may come into contact with one another and locked together, as shown in FIG. 9C. One or both hubs 214, 234 may be configured to releasably lock together through any method of mechanical attachment. For example, hubs 214, 234 may be threaded to screw onto one another, or hubs 214, 234 may be configured to be secured via an interference fit, or any other mechanical fastening method known in the art may be utilized. Furthermore, a gasket may be provided to fit in-between hubs 214, 234 to provide for a fluid-tight seal therebetween. Cooling hub 234 may be fluidly connected to a pump via inlet tube 242 and outlet tube 244. Once hubs 214, 234 have been secured together, cooling fluid may be introduced through inlet tube 242 and through hub 234 such that the fluid enters into lumen 220 to envelope and contact antenna 236 to cool antenna 236, if desired. The fluid may be removed from lumen 220 via outlet tube 244, which may also be in fluid communication with lumen 220 via hub 234. Once the procedure has been completed, the entire assembly may be removed from the tissue.

Yet another variation on antenna cooling assembly 250 may be seen in the side view in FIG. 10. In assembly 250, cooling jacket 256 may be modified to cover only the radiating portion 254 of the microwave antenna. Cooling jacket 256 may thus be configured to be shortened in length from, e.g., cooling jacket 108 described above, and may further omit a handle portion to form cooling channel 262 around radiating portion 254. Inlet tube 258 and outlet tube 260 may be incorporated with jacket 256 to provide the cooling fluid flow within cooling jacket 256. The remainder of antenna shaft 252 may remain uncovered by cooling jacket 256.

FIG. 11 shows another variation in cooling assembly 270 in which antenna shaft 272 may have cooling tube 276 coiled around at least a portion of shaft 272. Cooling tube 276 may have cooling fluid flowing therethrough via inlet tube 278 and outlet tube 280 connected to a pump. In the variation shown, tube 276 is coiled around a portion of antenna shaft 272 up to radiating portion 274. In an alternative variation, tube 276 may also be coiled around radiating portion 274, in which case tube 276, or the portion of tube 276 covering radiating portion 274, is preferably fabricated from a polymeric or plastic material. Furthermore, tube 276 may be coiled only over radiating portion 274. An optional covering or sheath, preferably made from a polymeric material, e.g., PTFE, Pebax®, etc., may be formed or fitted over the coiled tube 276 (or a portion of the coiled tube 276) to provide a lubricious surface for assembly 270 for insertion into tissue.

Another variation on the cooling assembly is shown in FIGS. 12A and 12B, which show side and cross-sectional views, respectively, of a loop antenna variation 290 configured to cool the antenna. This variation is shown for a microwave antenna having a looped antenna, but the principles are applicable to straight antenna probes, as will be described in further detail below. In assembly variation 290, antenna shaft 292 may have fluid outer tube 294 positioned within antenna shaft 292 and fluid inner tube 296 coaxially positioned within outer tube 294. The assembly of tubes 294, 296 may form inner conductor assembly 298 and each tube may extend through the length of antenna shaft 292 and beyond to form the curved antenna portion. The distal end of fluid inner tube 296 may terminate proximally of the distal end of fluid outer tube 294, which is preferably enclosed at its terminal end. The distal end of fluid inner tube 296 may also define an opening to allow for fluid communication between tubes 294, 296.

Fluid inner tube 296 may define an inflow lumen 300, as shown in FIG. 12B, and fluid outer tube 294 may define an outflow lumen 302 in the space between tubes 294, 296. Thus, cooling fluid may be circulated through the inner conductor 298 itself to cool the antenna during microwave energy transmission. Tubes 294, 296 may be formed from an electrically conductive material suitable for microwave transmission, e.g., stainless steel, platinum, gold, nickel, etc., or stainless steel plated with an electrically conductive material having a lower electrical resistivity than the stainless steel.

Aside from utilizing direct contact between the cooling fluid and the microwave antenna, other variations may employ cooling sheaths, such as the variation shown in FIGS. 13A to 13C, which show end, cross-sectional side, and perspective views, respectively, of cooling sheath assembly 310. Sheath assembly 310 may generally comprise main tubular member 312 which defines an antenna lumen 316 therethrough. Tubular member 312 may be fabricated of a polymeric or plastic material, as described above, and preferably defines a diameter sufficient to accommodate the shaft of a microwave antenna positioned within antenna lumen 316. Furthermore, tubular member 312 may be at least partially formed of a metallic material (preferably proximal to the radiating portion), or member 312 may be formed of a ceramic material. Tubular member 312 is preferably wide enough to allow for direct contact or close contact against an outer surface of the microwave antenna when the antenna is positioned within to facilitate the heat transfer. The tubular member 312 may also be formed of a material, e.g., heat-shrink polymers, which allow for tubular member 312 to conform to an outer surface of the microwave antenna to ensure close thermal contact. Alternatively, a thermally conductive and conformable material, such as a gel or fluid, may be poured or placed within the space, if present, between antenna lumen 316 and the inner wall of tubular member 312 to ensure consistent thermal contact between the two.

A coaxially positioned fluid tube 314, as seen in FIG. 13A, may be positioned around tubular member 312 and define fluid channel 322, as seen in the cross-sectional view of FIG. 13B. Fluid tube 314 may be formed as a common channel such that fluid contained therewithin envelopes or encompasses the outer surface of tubular member 312. Fluid tube 314 may also be varied in length to surround a majority of tubular member 312 or just a portion of it depending upon the desired cooling effects. Inlet tube 318 may be positioned within fluid channel 322 such that the distal end of inlet tube 318 is positioned near or at the distal end of fluid tube 314 while the distal end of outlet tube 320 may be positioned near or at the proximal end of fluid tube 314 to facilitate the heat transfer. Fluid tube 314 may be integrally fabricated with tubular member 312; however, fluid tube 314 may also be made of a material different from tubular member 312 and attached through one of any mechanical fastening methods. The distal end of fluid tube 314 and the distal end of tubular member 312 may be joined together; and the proximal end of fluid tube 314 may be attached, connected, or integrally formed with either the proximal end of tubular member 312 or at a predetermined location along an outer surface distal of the proximal end of tubular member 312. Thus, fluid channel 322 may be formed as a common circumferential fluid channel. If cooling sheath assembly 310 is positioned over only the shaft portion of a microwave antenna, assembly 310 may be made from a metallic material such as stainless steel. Alternatively, if assembly 310 is also configured to be positioned over the radiating portion of an antenna, the entire assembly 310, or at least the portion of the assembly 310 covering the antenna, is preferably made from a polymeric or plastic material, as described above. The distal end of assembly 310 may be formed into a tapered or atraumatic end 324 to prevent damage to surrounding tissue when assembly 310 is inserted into a patient.

FIG. 14A shows a side view of a cooling sheath assembly in one variation 330 used with a straight probe microwave antenna. As shown in this variation, assembly 330 may comprise cooling sheath 332 for placement over a length of antenna shaft 344. The radiating portion 342 is uncovered in this variation, although alternative sheath designs may be employed to entirely cover the radiating portion 342 as well. Assembly 330 may also comprise hub 334, through which inlet tube 338 and outlet tube 340 may be in fluid communication with sheath 332 to allow for circulation of the cooling fluid. An optional adjustable securing member, e.g., tightening knob 336, may be provided on hub 334, or directly on sheath 332, to prevent sheath 332 from moving relative to antenna shaft 344 by tightening knob 334 in a direction of the arrow shown. Knob 336 may be untightened as well to allow for removal or adjustment of sheath 332 over the antenna. Tightening knob 336 is shown as a rotatable securing mechanism, e.g., a tightening screw, however, other tightening methods as known in the art may be employed for securing sheath 332 to antenna shaft 344.

FIG. 14B shows a side view of the cooling sheath assembly of FIG. 14A in another variation 350 in which sheath 332 may be placed over the shaft 356 of a microwave antenna having a looped radiating portion 354. In variation 350, sheath 332 may be positioned over shaft 356 such that the portion of shaft 356 up to its distal end 352 is covered. Radiating portion 354 may remain uncovered in this variation. FIG. 14C shows the cooling sheath assembly in yet another variation 360 used with a looped microwave antenna configured to cool the radiating looped antenna portion. In this variation, sheath 332 may be used with a looped microwave antenna having an inner conductor configured to have cooling lumens integrated within, as shown and described for FIGS. 12A and 12B above. Alternatively, and as shown in FIG. 14C, a separate cooling balloon or sheath 362 may be formed to surround the radiating portion 354.

Balloon or sheath 362 is described in further detail in U.S. patent application Ser. No. 10/272,314, which has been incorporated herein above. Generally, balloon or sheath 362 may be disposed over the curved radiating portion 354 of the microwave antenna. Balloon or sheath 362 may be in a deflated state during the deployment of the antenna through sheath 332 and/or within the tissue, but once the curved antenna 354 has been desirably positioned, balloon 362 may be filled with the cooling fluid, e.g., chilled saline, water, etc., until it has sufficiently inflated. The size of balloon 362 may be varied according to the desired radiative effects (for impedance matching purposes), the length of radiating portion 354, as well as the type of tissue which the antenna is inserted within. Furthermore, the cooling fluid may be maintained statically within balloon 362 or it may be circulated in a manner as described above.

Another alternative for cooling a microwave antenna and/or preventing unnecessary tissue damage by a heated antenna feedline or shaft is seen in FIG. 15. The variation shown is a passively cooled balloon assembly 370 which may typically comprise microwave antenna shaft or feedline 372 with an inflatable balloon 374 positioned over a length of shaft 372. FIG. 15 shows balloon 374 in an inflated configuration over the microwave antenna. A balloon member 374, which may be inflatable with a liquid or gas (or combination of both) such as saline, water, air, nitrogen, etc., may be attached along microwave antenna shaft 372 at proximal attachment region 376 and distal attachment region 378 through any variety of attachment methods, e.g., adhesives, crimping, etc. Alternatively, a separate inflatable balloon may simply be placed over antenna shaft 372 and reside unattached to the microwave antenna. Balloon 374 may reside along shaft 372 to cover the portion of the shaft 372 which may come into contact with tissue when inserted into a patient. Distal attachment region 378 may be positioned proximally of antenna radiating portion 380 such that the entire radiating portion 380 is not covered by balloon 374. Alternatively, distal attachment region 378 may be positioned near or at the distal tip of the antenna so that a portion, or a majority of radiating portion 380, is at least partially covered by balloon 374.

In use, the microwave antenna may be advanced percutaneously or laparoscopically through the skin 382 of a patient to position antenna radiating portion 380 near or adjacent to tumor 384. Balloon 374 is preferably in a deflated configuration during the insertion through the skin 382, although balloon 374 may alternatively be inflated prior to or during insertion through skin 382, depending upon the circumstances. Once radiating portion 380 has been desirably positioned within the patient, balloon 374 may be inflated via an inlet tube prior to or during microwave energy transmission through the antenna. The inflation of balloon 374 may dilate the tissue 386 surrounding the shaft 372 and urge the tissue 386 out of contact with shaft 372. The radiating portion 380 may remain in direct contact with tumor 384 to effect microwave ablation treatment. Having balloon 374 move tissue 386 away from direct contact with antenna shaft 372 helps to prevent the tissue 386 from overheating or becoming ablated.

An alternative multi-balloon assembly 390 is shown in the side view of FIG. 16. The microwave antenna assembly 390 may be divided into several, i.e., two or more, regions along its shaft. For instance, first antenna region 392, second antenna region 394, and third antenna region 396 may each have a respective first balloon 400, second balloon 402, and third balloon 404 over each region such that each balloon 400, 402, 404 is adjacent to one another along the shaft outer surface. Each balloon 400, 402, 404 may be attached to the microwave antenna distal of connector hub 414 at first, second, third, and fourth attachment regions 406, 408, 410, 412, respectively, through one of any attachment methods as described above. A balloon may be positioned over radiating portion 398 or radiating portion 398 may be left exposed, as shown in the figure. The number of balloons in this example are merely illustrative and fewer or greater number of balloons may be utilized depending upon the desired configuration and cooling results. Moreover, each balloon 400, 402, 404 may be in fluid communication with one another in series such that all the balloons 400, 402, 404 may be inflated simultaneously. Alternatively, each balloon 400, 402, 404 may be individually inflatable such that a single balloon, or a combination of balloons, may be inflated while the other balloons may remain un-inflated, depending upon the desired cooling results. Moreover, each balloon may be inflatable with a liquid or gas (or combination of both) such as saline, water, air, nitrogen, etc., as described above. Furthermore, although a straight microwave antenna probe is shown in the figures, this is intended to be illustrative; alternatively, a microwave antenna having a curved radiating portion may also be utilized.

Aside from the use of inflatable balloons, alternative cooling methods and devices may comprise passive cooling sheaths, as shown in the exploded assembly 420 of FIG. 17. Assembly 420 may comprise a microwave antenna 422 having a radiating portion 424; in this example, a curved radiating portion 424. A tubular cooling pack 426 may define a lumen 428 into which the shaft of antenna 422 may be positioned. Both antenna 422 and cooling pack 426 may be positioned within a handle lumen 434 defined within handle 430. An optional insulation layer 432, e.g., foam, rubber, etc., may be disposed upon the inner surface of handle lumen 434 between cooling pack 426 and handle 430. Cooling pack 426 may simply be a plastic or polymeric tubular container of chilled or frozen water or saline, or another fluid which is preferably biocompatible, which may be cooled prior to use with the microwave antenna. Alternatively, cooling pack 426 may contain gels or chemicals which may be mixed (e.g., a mixture of water, urea, and ammonium chloride; alternatively, a mixture of potassium chloride or sodium nitrate and water, etc.) such that an endothermic reaction results and cooling of the antenna 422 may be achieved. Moreover, cooling pack 426 may be configured to come into intimate contact with the shaft of antenna 422 to ensure good thermal contact. Handle 430 may be molded from various materials, e.g., polymers, plastics, etc., and it may configured as a simple tubular handle. Alternatively, it may be ergonomically molded to allow for better handling by the user. The handle lumen 434 is preferably just wide enough to allow for the insertion of cooling pack 426 so that thermal contact between the two may occur. The cooling assembly 420 may be assembled prior to use with the antenna 422 such that the entire assembly is inserted into the tissue altogether; alternatively, it may be assembled within the tissue during tissue ablation.

Another variation may be seen in the side view of conformable cooling sheath assembly 440 in FIG. 18. The antenna shaft or feedline 442 of a microwave antenna may be inserted through a handle lumen 450 defined through conformable cooling sheath 440. Cooling sheath 440 may comprise a proximal handle portion 444 and a conformable portion 446 which may be configured to spread over and cool the skin surface 452 surrounding the area where the antenna shaft 442 has been inserted. Proximal handle portion 444 may be comprised of a polymeric or plastic material which may be adapted to maintain its configuration while conformable portion 446 may be comprised of a polymeric material adapted to spread out and conform against skin surface 452 over contact surface 448. Conformable sheath assembly 440 may be filled with any one of the liquids, gases, and/or chemical mixtures as described above.

Alternative cooling sheaths are further shown in FIGS. 20A to 21C. A cross-sectional side and end view of cooling sheath 460 is shown in FIGS. 19A and 19B, respectively, for comparison purposes. As shown, a simple cooling sheath 460, as described above, may define antenna lumen 462 therethrough. FIGS. 20A and 20B show cross-sectional side and end views of cooling sheath 470. Antenna lumen 474 may be defined through the length of sheath 470. Barriers 472 may be defined through the length of sheath 470 to divide the interior lumen into at least two separate volumes. A first defined volume 476 may hold a first chemical or liquid (e.g., water, saline, etc.) and second defined volume 478 may hold a second chemical or liquid (ammonium chloride, sodium nitrate, or potassium chloride, etc.). When a cooling effect is desired, sheath 470 may be flexed slightly such that barriers 472 may be broken or fractured within sheath 470 to allow for the mixing between the chemicals from first volume 476 and second volume 478 to result in an endothermic reaction.

Another alternative may be seen in the cross-sectional side views of FIGS. 21A and 21B and the end view of FIG. 21C of slidable sheath assembly 480. As shown in FIG. 21A, sheath assembly 480 may comprise an inner tube 484, which defines a first volume 492 for holding a first chemical or liquid, and a concentric outer tube 482, which defines a second volume 494 for holding a second chemical or liquid. The composition of the first chemical and/or second chemical contained in their respective volumes may include any of the chemicals and/or liquids mentioned above. Outer tube 482 may define a plurality of openings 488 over its inner surface and inner tube 484 may also define a plurality of openings 490 over its outer surface. Openings 488, 490 may be defined in each of their respective tubes such that when inner tube 484 and outer tube 482 are in a first misaligned configuration relative to one another, their respective openings are blocked, as shown in FIG. 21A. However, inner tube 484 and outer tube 482 may be moved longitudinally and/or rotationally relative to one another into a second aligned configuration such that openings 488, 490 may be aligned with one another and allow for the mixing of the respective chemicals to produce a cooling effect within antenna lumen 486, as shown in FIGS. 21B and 21C. These variations are intended to be illustrative and any variations on the number of openings or the manner in which openings may be aligned to allow for the mixture of various chemicals or liquids are intended to be within the scope of the invention.

Alternative variations in which the cooling sheath or tube may be integrated with or within the microwave antenna shaft are shown in the following FIGS. 22A to 22D. FIG. 22A shows a perspective view of a portion of a microwave antenna shaft assembly 500 in which outer tubing 508 may be formed as an integral part of the microwave antenna. The antenna is shown as comprising, in part, outer conductor 502 coaxially surrounding inner conductor 504 with dielectric 506 disposed therebetween. Outer tubing 508, which may be comprised of a metallic, e.g., stainless steel, or polymeric material, as described above, may surround the length, or at least a partial length of the microwave antenna. Outer tubing 508 may define a cooling lumen 510 between the outer conductor 502 through which a cooling fluid may be pumped through or simply filled.

FIG. 22B shows another cooling tube variation 520 in which outer tubing 522 may surround the microwave antenna, as in assembly 500 of FIG. 22A. Tubing 522, however, may include a barrier or divider 524 which separates the cooling lumen into at least a first lumen 526 and a second lumen 528, which may act as inlet and outlet lumens, respectively, for a cooling fluid to be flowed through. Divider 524 may be formed of the same or similar material as outer conductor 502 and/or outer tubing 522. FIG. 22C shows yet another variation 530 in which outer tube 532 may comprise a number of longitudinally formed dividers 534, 536, 538, 540, and 542 to create a number of corresponding cooling lumens 544, 546, 548, 550, and 552 in the space between outer conductor 502 and outer tubing 532. The cooling lumens may be utilized as inlet lumens or outlet lumens or various combinations thereof depending upon the desired cooling results. The number of dividers and cooling lumens is intended merely to be illustrative of the various combinations and numbers of cooling lumens which may be formed.

FIG. 22D shows yet another variation 560 in which cooling lumens may be formed within the space between inner conductor 502 and outer conductor 504, where a dielectric material is typically located. In this variation, longitudinally defined dividers 564, 566, 568, 570, and 572 may be formed of an electrically non-conductive material, e.g., polymers, to divide the space into a number of corresponding cooling lumens 574, 576, 578, 580, and 582. An optional cooling tube 562 may be utilized and positioned over outer conductor 502. As above, the cooling lumens may be utilized as inlet lumens or outlet lumens or various combinations thereof depending upon the desired cooling results. Moreover, the number of dividers and cooling lumens is intended merely to be illustrative and not limiting in scope.

In certain variations of the microwave antenna, an electrical choke may be utilized to improve the energy focus of an antenna assembly. The electrical choke and its use is described in further detail in U.S. patent application Ser. Nos. 10/052,848 and 10/272,058, which have been incorporated herein by reference above. Generally, the choke may be disposed on the antenna proximally of the radiating section. The choke is preferably placed over a dielectric material which may be disposed over the antenna. The choke is preferably a conductive layer and may be further covered by a tubing or coating. A cross-sectional view of a triaxial antenna 590 may be seen in FIG. 23A having inner conductor 592 and outer conductor 594 with dielectric 596 disposed therebetween. The choke layer 598 may be seen formed over outer conductor 594 with dielectric 600 disposed between the two layers. FIG. 23B shows a cooling choke variation 610 in which a number of longitudinally defined dividers 612, 614, 616, 618, and 620 may form a number of corresponding cooling lumens 622, 624, 626, 628, and 630. The dividers may be formed of an electrically non-conductive material, e.g., polymers, and the cooling lumens may be utilized as inlet lumens or outlet lumens or various combinations thereof depending upon the desired cooling results.

Cooling sheaths or jackets, as described above, may be varied or tuned to match the requisite cooling for a given length of a microwave antenna. A typical microwave antenna may generally be divided into at least three different regions along the length of its shaft. For instance, in FIG. 24, a side view of microwave antenna 640 may be seen divided into a first region 642, second region 644, and third region 646. First region 642 may generally comprise the radiating antenna or the region of active heating during microwave ablation. It may be desirable to cool this region 642 to maintain optimal energy delivery by preventing the surrounding tissue from charring, which in turn may change the effective wavelength. Second region 644 is generally the portion of antenna 640 which is in contact with the tissue surrounding a tumor or lesion to be ablated. This region 644 typically becomes hot from ohmic heating and some conductive heating from first region 642. It may be desirable to allow second region 644 to heat up in certain tissue regions where coagulation of the insertion tract may be desirable. However, it may also be desirable to cool this region 644 in other applications to protect surrounding sensitive tissue structures from heat damage. Finally, third region 646 is generally the portion of antenna 640 which comes into contact with the skin of a patient. This region 646 typically heats up because of ohmic heating and it is generally desirable to keep this region cool when used in percutaneous or laparoscopic procedures to prevent heat damage to the skin surface. In other procedures, such as in applications where lesions are located deep within the tissue, it may be desirable to allow region 646 to become heated to allow for the coagulation of the insertion tract.

Accordingly, a multi-zone cooling assembly 650, such as the variation shown in FIG. 25, may be utilized to take advantage of optionally cooling multiple regions along the length of a microwave antenna. Cooling jacket 652 may surround the length of microwave antenna 660 and define a smooth outer surface for insertion into tissue. The interior of cooling jacket 652 may define a distal first cooling region 654, second cooling region 656, and a proximal third cooling region 658. These cooling regions 654, 656, 658 may correspond to and envelope the various regions of antenna 660, e.g., first region 662 may be positioned within first cooling region 654, second region 664 may be positioned within second cooling region 656, and third region 666 may be positioned within third cooling region 658. Each of the cooling regions 654, 656, 658 may be divided from one another when antenna 660 is positioned within cooling jacket 652 via, e.g., electrically insulative gaskets such as rubber or polymers, to prevent fluid communication between the adjacent cooling regions. For instance, first divider 680 may separate first and second cooling regions 654, 656; second divider 682 may separate second and third cooling regions 656, 658; and third divider 684 may separate third cooling region 658 from the remainder of cooling jacket 652.

Each individual cooling region may thus be maintained at a different cooling rate than from an adjacent cooling region, depending upon the desired cooling profile. To maintain the differential cooling regions, any of the various cooling methods described herein may be utilized; in particular, each cooling region may utilize its own fluid inlet and outlet tubes. For instance, as shown in the figure, first cooling region 654 may have a first inlet tube 668 and first outlet tube 670; second cooling region 656 may have a second inlet tube 672 and second outlet tube 674; and third cooling region 658 may have a third inlet tube 676 and third outlet tube 678. Each pair of inlet and outlet tubes may be connected to separate pumps or they may be connected to a common pump with individually controlled valves for maintaining each cooling region at a different flow rate, if desired. The number of cooling regions is merely illustrative in this example and is not intended to be limiting.

FIG. 26A shows yet another variation in which the diameters of the inner conductor may be modified so that proximal portions of the inner conductor functions as a heat sink to facilitate conductive cooling of the microwave antenna. Multi-diameter cable assembly 690 may comprise an inner conductor assembly 692 having a proximal portion 694 with a first diameter and a distal portion 696 with a second diameter smaller than the first diameter. The two portions 694, 696 may be joined via a tapered portion 698. The inner conductor assembly 692 may be surrounded by outer conductor 700, which may also similarly taper from a first portion having a diameter, e.g., 0.141 inches, down into a second portion having a diameter, e.g., 0.070 inches, smaller that the first portion to facilitate insertion into tissue. This dual-diameter inner conductor assembly may not only increase the pushability of the antenna portion into the tissue, but may also allow proximal portion 694 to function as a heat sink and to help conduct heat away proximally from the radiating portion. Moreover, having a larger cable helps to improve the power handling capabilities which in turn helps to facilitate a decrease in the generation of high temperatures which may be harmful to healthy tissue. The tapered portion 698 may be created, e.g., by soldering the two portions 694, 696 together.

FIGS. 26B and 26C show cross-sectional side views of optional transitional diameters which may be utilized for the inner conductors. As shown in FIG. 26B, first portion 102 may have a standard diameter of, e.g., 0.141 inches, while second distal portion 704 may transition down to a portion having a diameter of, e.g., 0.070 inches. FIG. 26C shows another example where first portion 102 may transition down to a second distal portion 706 having a diameter of, e.g., 0.085 inches. Other variations may utilize other diameters and these examples are shown for illustrative purposes only.

An example of the cooling capacity of some of the cooling variations described above is shown in the corresponding plots in FIGS. 27 and 28. FIG. 27 shows a plot 710 over time of the heating which may occur in a microwave antenna which is uncooled. The temperature measurements were taken along a middle portion of a microwave antenna having a diameter of about 0.047 inches. At 60 W of power, the measured temperature reaches approximately 100° C. in less than 9 seconds. FIG. 28 shows an example in plot 720 of the cooling capacity of the same microwave antenna utilizing a cooling sheath as shown in FIGS. 13A to 13C, as described above. With the power initially off, temperature measurements were taken on the surface of the cooling sheath above the same location where measurements were taken on the microwave antenna. Slope 722 indicates antenna heating at 60 W of power with no cooling fluid being pumped through the sheath. Slope 724 indicates where the cooling fluid is being circulated through the sheath. Measurements indicated that the temperature of the antenna returned to normal levels within 6-8 seconds from when the cooling fluid was circulated. Cooling fluid was then shut off and a temperature rise 726 may be seen again. Slope 728 indicates again where the fluid is restarted to circulate within the sheath.

This invention has been described and specific examples of the invention have been portrayed. The use of those specifics is not intended to limit the invention in any way. It is also contemplated that combinations of features between various examples disclosed above may be utilized with one another in other variations. Additionally, to the extent there are variations of the invention with are within the spirit of the disclosure and yet are equivalent to the inventions found in the claims, it is our intent that this patent will cover those variations as well.

We claim:

1. A cooling system for use with a microwave antenna, comprising:

a cooling jacket adapted to at least partially surround a microwave antenna and defining a fluid channel around at least a portion of the microwave antenna, the cooling jacket further defining at least a first and a second region longitudinally adjacent to and separate from one another, the first region adapted to retain cooling fluid from at least one source that is in fluid contact with a first portion of the microwave antenna, and the second region adapted to retain cooling fluid from at least one source that is in fluid contact with a second portion of the microwave antenna; and wherein the cooling jacket is further adapted to circulate a cooling fluid through the fluid channel such that at least a portion of the microwave antenna is in direct fluid contact with the cooling fluid and wherein the microwave antenna comprises a distal tip configured to be advanced percutaneously through tissue.

2. The system of claim 1 further comprising at least one inlet lumen and at least one outlet lumen each in fluid communication with the cooling jacket for circulating the cooling fluid therethrough.

3. The system of claim 2 wherein a distal end of the inlet lumen is positioned near or at a distal end of the microwave antenna.

4. The system of claim 2 wherein a distal end of the outlet lumen is positioned proximally of the microwave antenna distal end.

5. The system of claim 2 wherein the inlet lumen is defined along an outer surface of the cooling jacket.

6. The system of claim 2 wherein the inlet lumen is defined within a wall of the cooling jacket.

7. The system of claim 1 further comprising a tip at a distal end of the cooling jacket.

8. The system of claim 7 wherein the tip is tapered.

9. The system of claim 7 further comprising a power generator in electrical communication with the tip.

10. The system of claim 7 wherein a distal end of the microwave antenna is securable to a proximal portion of the tip.

11. The system of claim 10 wherein the tip is adapted to be in electrical communication with the distal end of the microwave antenna.

12. The system of claim 1 further comprising a handle assembly for attachment to a proximal end of the cooling jacket.

13. The system of claim 12 wherein the handle assembly defines at least one lumen therethrough which is in fluid communication with the cooling jacket.

14. The system of claim 1 further comprising a pump for circulating the cooling fluid through the cooling jacket.

15. The system of claim 1 wherein the cooling fluid comprises a liquid, gas, or combination thereof.

16. The system of claim 15 wherein the liquid comprises water or saline.

17. The system of claim 15 wherein the gas is selected from the group consisting of nitrous oxide, nitrogen, and carbon dioxide.

18. The system of claim 1 further comprising a temperature sensor for sensing a temperature of the system.

19. The system of claim 1 further comprising an introducer which is insertable into the cooling jacket.

20. The system of claim 1 wherein the cooling jacket is configured in length to match a radiating portion of the microwave antenna.

21. The system of claim 1 wherein the first region is adapted to retain the cooling fluid from a first source in fluid contact with a first portion of the microwave antenna, and the second region is adapted to retain cooling fluid from a second source in fluid contact with a second portion of the microwave antenna.

22. The system of claim 21 wherein the cooling fluid from the first source is maintained at a first temperature and the cooling fluid from the second source is maintained at a second temperature.

23. The system of claim 21 wherein the cooling jacket defines a plurality of additional regions adjacent to and separate from one another.

24. The system of claim 1 wherein the first region is adapted to retain the cooling fluid from a first source in fluid contact with a first portion of the microwave antenna, and the second region is adapted to retain cooling fluid from the first source in fluid contact with a second portion of the microwave antenna.

* * * * *